US008722625B2

(12) United States Patent
Culiat

(10) Patent No.: US 8,722,625 B2
(45) Date of Patent: May 13, 2014

(54) TREATMENT OF CARDIOVASCULAR DISORDERS USING THE CELL DIFFERENTIATION SIGNALING PROTEIN NELL1

(75) Inventor: Cymbeline T. Culiat, Oak Ridge, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 877 days.

(21) Appl. No.: 12/284,667

(22) Filed: Sep. 24, 2008

(65) Prior Publication Data

US 2009/0087415 A1 Apr. 2, 2009

Related U.S. Application Data

(60) Provisional application No. 60/995,854, filed on Sep. 28, 2007, provisional application No. 61/079,446, filed on Jul. 10, 2008.

(51) Int. Cl.
*A61K 38/00* (2006.01)
*A61K 38/02* (2006.01)
*A61K 48/00* (2006.01)

(52) U.S. Cl.
USPC .................. 514/16.4; 514/44 R; 514/1.1

(58) Field of Classification Search
USPC ....................... 514/16.4, 1.1, 44 R
See application file for complete search history.

(56) References Cited

U.S. PATENT DOCUMENTS

| 7,052,856 | B2 | 5/2006 | Ting |
| 7,910,542 | B2 | 3/2011 | Culiat |
| 2004/0186423 | A1 | 9/2004 | Cafferata |
| 2006/0025367 | A1 | 2/2006 | Simari |
| 2006/0053503 | A1 | 3/2006 | Culiat et al. |
| 2006/0111313 | A1 | 5/2006 | Ting et al. |
| 2006/0228392 | A1 | 10/2006 | Ting |
| 2006/0292670 | A1 | 12/2006 | Ting et al. |
| 2007/0134291 | A1 | 6/2007 | Ting et al. |
| 2009/0142312 | A1 | 6/2009 | Culiat |
| 2011/0236325 | A1 | 9/2011 | Culiat et al. |

FOREIGN PATENT DOCUMENTS

| WO | 02/100426 A1 | 12/2002 |
| WO | 2004/072100 A1 | 8/2004 |
| WO | 2009/042859 A1 | 4/2009 |
| WO | 2011091244 | 7/2011 |

OTHER PUBLICATIONS

Liu, L. et al., "Characterizing the Role of the Nell1 Gene in Cardiovascular Development", *Office of Workforce Development for Teachers and Scientist*, (2007), Abstract.
Tsutsumi, S. et al., "The Novel Gene Encoding a Putative Transmembrane Protein is Mutated in Gnathodiaphyseal Dysplasia (GDD)", *Am. J. Hum. Genet* 74: 1255-1261 (2004).
Zhang, X. et al., "Nell-1 induces acrania-like cranioskeletal deformities during mouse embryonic development", *Lab Invest* 86(7): 633-644 (2006).
Zhang, X. et al., "Overexpression of Nell-1, a craniosynostosis-associated gene, induces apoptosis in osteoblasts during craniofacial development", *J Bone Miner Res.* 18(12): 2126-2134 (2003).
Ting, K. et al., "Human NELL-1 expressed in unilateral coronal synostosis", *J Bone Miner Res.* 14(1): 80-90 (1999).
Aghaloo, T. et al., "Nell-1-induced bone regeneration in calvarial defects", *Am J Pathol.* 169(3): 903-915 (2006).
Zhang, X. et al., "Craniosynostosis in transgenic mice overexpressing Nell-1 ", *J Clin Invest.* 110(6): 861-870 (2002).
Cowan, C.M. et al., "Nell-1 induced bone formation within the distracted intermaxillary suture", *Bone* 38(1): 48-58 (2006).
Desai, J. et al., "Nell1-deficient mice have reduced expression of extracellular matrix proteins causing cranial and vertebral defects", *Hum Mol Genet.* 15(8): 1329-1341 (2006).
Maeda, K. et al., "Brain specific human genes, NELL1 and NELL2, are predominantly expressed in neuroblastoma and other embryonal neuroepithelial tumors", *Neurol Med Chir (Tokyo)* 41(12): 582-588 (2001).
Luce, M. J. et al., "The neuronal EGF-related genes NELL1 and NELL2 are expressed in hemopoietic cells and developmentally regulated in the B lineage", *Gene* 231(1-2): 121-126 (1999).
Kuroda, S. et al., "Biochemical characterization and expression analysis of neural thrombospondin-1-like roteins Nell1 and NELL2", *Biochem Biophys Res Commun.* 265(1): 79-86 (1999).
Watanabe, T.K. et al., "Cloning and characterization of two novel human cDNAs (NELL1 and NELL2) encoding proteins with six EGF-like repeats", *Genomics* 38: 273-276 (1996).
Shen, Y. et al., "Knock Down of NELL2 in Wilms' Tumor Cell Line", *Journal of the William Jarvie Society*, vol. 49, p. 41(2006), Abstract.
Santini, M. P. et al., "Signalling pathways in cardiac regeneration", *Novartis Found Symp.* 274: 228-238 (2006).
Rubart, M. et al., "Cell-based approaches for cardiac repair", *Ann NY Acad Sci.* 1080: 34-38 (2006).
Ott, H. C. et al., "From cardiac repair to cardiac regeneration—ready to translate?", *Expert Opin Biol Ther.* 6(9): 867-878 (2006).
Rosenthal, N. et al., "Growth factor enhancement of cardiac regeneration", *Cell Transplant* 15(Suppl1): S41-S45(2006).
Kuroda, S. et al., "Involvement of epidermal growth factor-like domain of NELL proteins in the novel protein-protein interaction with protein kinase C.", *Biochem Biophys Res Commun.* 265(3): 752-757 (1999).
Haider, H. K.H., "Bone marrow cells for cardiac regeneration and repair: current status and issues", *Expert Rev Cardiovasc Ther.* 4(4): 557-568 (2006).
Orlic, D. et al., "Transplanted Adult Bone Marrow Cells Repair Myocardial Infarcts in Mice", *Ann N Y Acad Sci* 938(1):221-230(2001).
Lu, S. S. et al., "The osteoinductive properties of Nell-1 in a rat spinal fusion model", *The Spine Journal* 7(1): 50-60 (2007).
The Reporter, No. 78 (Jun. 2006), published by Oak Ridge National Laboratory, accessible on line at http://www.ornl.gov/info/reporter/no78/june06 dw.htm.

(Continued)

*Primary Examiner* — Taeyoon Kim
(74) *Attorney, Agent, or Firm* — Edna I. Gergel

(57) ABSTRACT

It has been identified in accordance with the present invention that Nell1 is essential for normal cardiovascular development by promoting proper formation of the heart and blood vessels. The present invention therefore provides therapeutic methods for treating cardiovascular disorders by employing a Nell1 protein or nucleic acid molecule.

14 Claims, 6 Drawing Sheets

(56) References Cited

OTHER PUBLICATIONS

Abstract entitled "Characterizing the Role of the Nell1 Gene in Cardiovascular Development" from the 2007 *American Association for the Advancement of Science (AAAS) Annual Meeting* entitled "Science and Technology for Sustainable Well-Being" that occurred on Feb. 15-19, 2007, pp. A125.

Aghaloo, T. et al., "A Study of the Role of Nell-1 Gene Modified Goat Bone Marrow Stromal Cells in Promoting New Bone Formation" Molecular Therapy (2007) pp. 1872-1880, vol. 15, No. 10.

Bareggi, R. et al., "Protein Kinase C (PKC) Isoenzymes Exhibit Specific Expression in the Vertebral Column of Human Fetuses" Journal of Biological Reseasrch (1995) pp. 83-91, vol. LXXI.

Cowan, et al., "Synergistic Effects of Nell-1 and BMP-2 on the Osteogenic Differentiation of Myoblasts," Journal of Bone Mineral Reseasrch (2007) pp. 918-930, vol. 22.

Culiat, C.T. et al., "Nell1: A Candidate Gene for ENU-Induced Recessive Lethal Mutations at the 17R6 Locus and Potential Mouse Models for Human Neonatal Unilateral . . . ," International Mammalian Genome Society, 15th International Mouse Genome Conference (2001).

Desai, J. et al., "Nell1, A Gene Coding for a Novel PKC-Binding Protein Is a Candidate for Late-Gestation Recessive Lethal Mutations at the I7R6 Locus" 16th International Mouse Genome Conference, San Antonio, TX, Presentation on Nov. 17-21, 2002 (Abstract).

Desai, J. et al., "Characterization of Mouse Nell1: A Gene Coding for a Novel PKC-Binding Protein" Women in Science Meeting, ORNL, Oak Ridge, TN, Presentation on May 1, 2006 (Abstract).

Lee, M. et al. "Effect of Nell-1 Delivery on Chondrocyte Proliferation and Cartilaginous Exracellular Matrix Deposition" Tissue Eng. Part A (2010) pp. 1791-1800, vol. 16, No. 5.

Liu, L. et al., "Characterizing the Role of the Nell1 Gene in Cardiovascular Development" Oak Ridge Science Semester Poster Presentation, ORNL, Oak Ridge, TN, Presentation on Aug. 11, 2006 (Poster).

Rinchik, E.M. et al., "Functional Annotation of Mammalian Genomic DNA Sequence by Chemical Mutagenesis: A Fine-Structure Genetic Mutation Map of a 1-to 2-cM Segment of Mouse Chromosome 7 Corresponding to Human Chromosome 11p14p15" PNAS (2002) pp. 844-849, vol. 99, No. 2.

Chen, W. et al., "Nfatc2 is a Primary Response Gene of Nell-1 Regulating Chondrogenesis in ATDC5 Cells" Journal of Bone and Mineral Research (2011) pp. 1230-1241, vol. 26, No. 6.

Liu et al., "Characterizing the Role of the Nell1 Gene in Cardiovascular Development," U.S. Department of Energy Journal of Undergraduate Research, 2007, pp. 63-70.

Franke et al., "Systematic Association Mapping Identifies NELL1 as a Novel IBD Disease Gene," PLoS One, 2007, pp. 1-13, vol. 8(e691) and supplemental documents.

Culiat et al., "Nell1: A Candidate Gene for ENU-Induced Recessive Lethal Mutations at the 17R6 Locus and Potential Mouse Models for Human Neonatal Unilateral Coronal Synostosis (UCS)," Jan. 27-31, 2002 (Abstract).

Desai et al., "Nell1-Deficient Mice Have Reduced Expression of Extracellular Matrix Proteins Causing Cranial and Vertebral Defects," 20th International Mouse Genome Conference, Charleston, SC, Presentation on Nov. 14, 2006 (Abstract).

```
>ref|NP_001032995.1| UG protein kinase C-binding protein NELL1 [Mus musculus
 gb|AAV41488.1| UG protein kinase C-binding protein NELL1 [Mus musculus]
Length=810

Score = 1431 bits (3704),  Expect = 0.0, Method: Composition-based stats.
                                                    , Gaps = 0/810 (0%)

Query  1    MPMDLILVVWFCVCTARTVVGFGMDPDLQMDIVTELDLVNTTLGVAQVSGMHNASKAFLF   60
            MPMD+ILV+WFCVCTARTV+GFGMDPDLQMDI+TELDLVNTTLGV QV+G+HNASKAFLF
Sbjct  1    MPMDVILVLWFCVCTARTVLGFGMDPDLQMDIITELDLVNTTLGVTQVAGLHNASKAFLF   60

Query  61   QDIEREIHAAPHVSEKLIQLFQNKSEFTILATVQQKPSTSGVILSIRELEHSYFELESSG   120
            QD++REIH+APHVSEKLIQLF+NKSEFT LATVQQKPSTSGVILSIRELEHSYFELESSG
Sbjct  61   QDVQREIHSAPHVSEKLIQLFRNKSEFTFLATVQQKPSTSGVILSIRELEHSYFELESSG   120

Query  121  LRDEIRYHYIHNGKPRTEALPYRMADGQWHKVALSVSASHLLLHVDCNRIYERVIDPPDT   180
             R+EIRYHYIH GKPRTEALPYRMADGQWHKVALSVSASHLLLHVDCNRIYERVIDPP+T
Sbjct  121  PREEIRYHYIHGGKPRTEALPYRMADGQWHKVALSVSASHLLLHVDCNRIYERVIDPPET   180

Query  181  NLPPGINLWLGQRNQKHGLFKGIIQDGKIIFMPNGYITQCPNLNHTCPTCSDFLSLVQGI   240
            NLPPG NLWLGQRNQKHG FKGIIQDGKIIFMPNG+ITQCPNLN TCPTCSDFLSLVQGI
Sbjct  181  NLPPGSNLWLGQRNQKHGFFKGIIQDGKIIFMPNGFITQCPNLNRTCPTCSDFLSLVQGI   240

Query  241  MDLQELLAKMTAKLNYAETRLSQLENCHCEKTCQVSGLLYRDQDSWVDGDHCRNCTCKSG   300
            MDLQELLAKMTAKLNYAETRL QLENCHCEKTCQVSGLLYRDQDSWVDGD+CRNCTCKSG
Sbjct  241  MDLQELLAKMTAKLNYAETRLGQLENCHCEKTCQVSGLLYRDQDSWVDGDNCRNCTCKSG   300

Query  301  AVECRRMSCPPLNCSPDSLPVHIAGQCCKVCRPKCIYGGKVLAEGQRILTKSCRECRGGV   360
            AVECRRMSCPPLNCSPDSLPVHI+GQCCKVCRPKCIYGGKVLAEGQRILTK+CRECRGGV
Sbjct  301  AVECRRMSCPPLNCSPDSLPVHISGQCCKVCRPKCIYGGKVLAEGQRILTKTCRECRGGV   360

Query  361  LVKITEMCPPLNCSEKDHILPENQCCRVCRGHNFCAEGPKCGENSECKNWNTKATCECKS   420
            LVKITE CPPLNCSEKDHILPENQCCRVCRGHNFCAE PKCGENSECKNWNTKATCECK+
Sbjct  361  LVKITEACPPLNCSEKDHILPENQCCRVCRGHNFCAEAPKCGENSECKNWNTKATCECKN   420

Query  421  GYISVQGDSAYCEDIDECAAKMHYCHANTVCVNLPGLYRCDCVPGYIRVDDFSCTEHDEC   480
            GYISVQG+SAYCEDIDECAAKMHYCHANTVCVNLPGLYRCDC+PGYIRVDDFSCTEHD+C
Sbjct  421  GYISVQGNSAYCEDIDECAAKMHYCHANTVCVNLPGLYRCDCIPGYIRVDDFSCTEHDDC   480

Query  481  GSGQHNCDENAICTNTVQGHSCTCKPGYVGNGTICRAFCEEGCRYGGTCVAPNKCVCPSG   540
            GSGQHNCD+NAICTNTVQGHSCTC+PGYVGNGT+C+AFCEEGCRYGGTCVAPNKCVCPSG
Sbjct  481  GSGQHNCDKNAICTNTVQGHSCTCQPGYVGNGTVCKAFCEEGCRYGGTCVAPNKCVCPSG   540

Query  541  FTGSHCEKDIDECSEGIIECHNHSRCVNLPGWYHCECRSGFHDDGTYSLSGESCIDIDEC   600
            FTGSHCEKDIDEC+EG +ECHNHSRCVNLPGWYHCECRSGFHDDGTYSLSGESCIDIDEC
Sbjct  541  FTGSHCEKDIDECAEGFVECHNHSRCVNLPGWYHCECRSGFHDDGTYSLSGESCIDIDEC   600

Query  601  ALRTHTCWNDSACINLAGGFDCLCPSGPSCSGDCPHEGGLKHNGQVWTLKEDRCSVCSCK   660
            ALRTHTCWNDSACINLAGGFDCLCPSGPSCSGDCPHEGGLKHNGQVW L+EDRCSVCSCK
Sbjct  601  ALRTHTCWNDSACINLAGGFDCLCPSGPSCSGDCPHEGGLKHNGQVWILREDRCSVCSCK   660

Query  661  DGKIFCRRTACDCQNPSADLFCCPECDTRVTSQCLDQNGHKLYRSGDNWTHSCQQCRCLE   720
            DGKIFCRRTACDCQNP+ DLFCCPECDTRVTSQCLDQ+G KLYRSGDNWTHSCQQCRCLE
Sbjct  661  DGKIFCRRTACDCQNPNVDLFCCPECDTRVTSQCLDQSGQKLYRSGDNWTHSCQQCRCLE   720

Query  721  GEVDCWPLTCPNLSCEYTAILEGECCPRCVSDPCLADNITYDIRKTCLDSYGVSRLSGSV   780
            GE DCWPL CP+LSCEYTAI EGECCPRCVSDPCLADNI YDIRKTCLDS G+SRLSG+V
Sbjct  721  GEADCWPLACPSLSCEYTAIFEGECCPRCVSDPCLADNIAYDIRKTCLDSSGISRLSGAV   780

Query  781  WTMAGSPCTTCKCKNGRVCCSVDFECLQNN   810
            WTMAGSPCTTC+CKNGRVCCSVD  CL+NN
Sbjct  781  WTMAGSPCTTCQCKNGRVCCSVDLVCLENN   810
```

FIGURE 5

TREATMENT OF CARDIOVASCULAR DISORDERS USING THE CELL DIFFERENTIATION SIGNALING PROTEIN NELL1

CROSS REFERENCE TO RELATED APPLICATIONS

This application asserts the priority of U.S. provisional application Ser. No. 60/995,854 filed Sep. 28, 2007, and U.S. provisional application Ser. No. 61/079,446, filed Jul. 10, 2008, the contents of which are incorporated herein by reference.

STATEMENT REGARDING FEDERALLY SPONSORED RESEARCH

This invention was made with Government support under Contract No. DE-AC05-00OR22725 between the United States Department of Energy and UT-Battelle, LLC. The Government has certain rights in this invention.

FIELD OF THE INVENTION

The present invention relates in general to therapeutic methods for treating cardiovascular disorders. More specifically, the present invention relates to therapeutic treatments of cardiovascular disorders by employing the cell differentiation signaling protein Nell1, as well as functional derivatives thereof.

BACKGROUND OF THE INVENTION

Despite many available methods of treatment, cardiovascular disease is one the major causes of death each year in the U.S. Thus, there is still a need for more effective agents to prevent and treat cardiac tissue injury, especially cardiac tissue injury resulting from ischemia/reperfusion.

The Nell1 gene codes for a secreted trimeric protein that stimulates bone and cartilage precursor cells (osteoblasts and chondrocytes) to differentiate into mature bone and cartilage tissue (Zhang et al., 2002; Desai et al., 2006). Nel-1 is a protein kinase C (PKC) β-binding protein. The Nell1 cDNA and amino acid sequences from a variety of mammalian species, including human, rat and mouse, have been reported.

Overexpression of Nell1 has been reported to cause premature fusion of the growing cranial bone fronts, resulting in craniosynostosis in humans and transgenic mice carrying a rat Nell1 transgene. A Nell1 knock-out mouse was also shown to exhibit several bone- and cartilage-related defects. There has been no characterization, however, of the impact of Nell1, if any, on cardiovascular development.

SUMMARY OF THE INVENTION

It has been identified in accordance with the present invention that Nell1 is essential for normal cardiovascular development by promoting proper formation of the heart and blood vessels. The present invention therefore provides therapeutic methods for treating cardiovascular disorders by employing a Nell1 protein, functional derivatives thereof or nucleic acid molecule.

Cardiovascular disorders or conditions contemplated by the present invention are diseases that involve the heart or blood vessels (arteries and veins), including in particular myocardial infarction (or "MI"). By treating a cardiovascular disorder or condition with the present methodology, the disorder is prevented or is delayed; or alternatively, its progression is slowed down, the extent of the injury is reduced, and the recovery is accelerated.

In one embodiment, the present invention provides a method of treating a cardiovascular disorder by administering a Nell1 protein or functional derivatives thereof to a subject in need of the treatment. Nell1 proteins suitable for use in the present method include wild type Nell1 proteins from any mammalian species, as well as functional derivatives thereof. Nell1 proteins, as well as functional derivatives thereof, can be recombinantly produced or purified from a mammalian body or tissue.

In another embodiment, the present invention provides a method of treating a cardiovascular disorder by administering a nucleic acid molecule encoding a Nell1 protein to a subject in need of the treatment. The nucleic acid molecule can be provided in an expression vector, including viral vectors and non-viral vectors, suitable for effecting the expression of the Nell1 protein in the targeted tissue or cells.

In accordance with the present invention, a Nell1 protein, functional derivatives thereof, or nucleic acid molecule can be combined with an appropriate pharmaceutically acceptable carrier for administration. Administration can be conducted in any practical and convenient manner, including by ingestion, injection or implantation, for example.

In a specific embodiment, a Nell1 protein, functional derivatives thereof, or Nell1-encoding nucleic acid molecule is used in combination with cell-based therapy for the repair and regeneration of damaged cardiac muscles and blood vessels. For example, a Nell1 protein, functional derivatives thereof, or Nell1-encoding nucleic acid molecule can be administered together with cardiomyocytes for repopulation of cells in the injured site. Alternatively, a Nell1 protein, functional derivatives thereof, or Nell1-encoding nucleic acid molecule can be administered together with stem cells isolated from adult bone marrow for regeneration of damaged cardiac muscles and blood vessels.

BRIEF DESCRIPTION OF THE DRAWINGS

FIG. 5 provides an alignment of the human (SEQ ID NO: 2) and murine (SEQ ID NO: 4) Nell1 proteins. The functional domains of the human Nell1 protein are found in the essentially same regions as those identified in the murine Nell1 protein.

DETAILED DESCRIPTION OF THE INVENTION

Figures 1A, 1B:
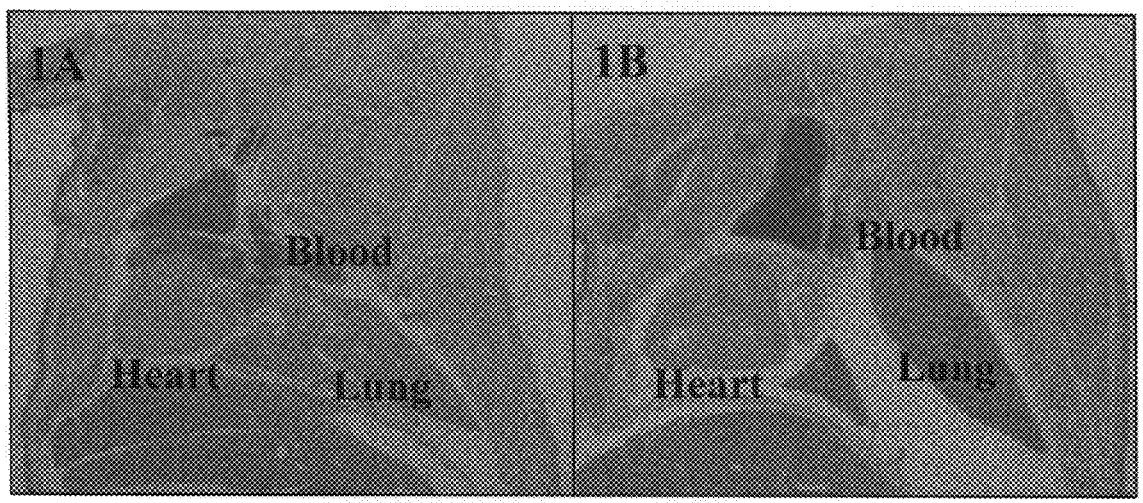
FIGS. 1A-1B show the cardiovascular defects in mice without Nell1 function (Nell1$^{6R}$ mutation). Homozygote fetuses at E18 days of gestation (Top) show decreased blood circulation (arrows) and unexpanded lungs compared to heterozygotes (bottom) and wild type animals (not shown). Fetuses were unable to breathe after birth or after caesarean recovery.

The present invention relates to therapeutic methods for treating cardiovascular conditions or disorders by employing the cell differentiation signaling protein Nell1, as well as functional derivatives thereof.

The present invention is based on the surprising discovery by the inventor that the Nell1 protein is essential for normal cardiovascular development by promoting proper formation of the heart and blood vessels. The inventor discovered that loss of Nell1 resulted in several tissue and organ changes typical of cardiac muscle injury, including heart enlargement, tissue hypertrophy, decreased blood vessel formation and blood circulation. The inventor observed that microscopic examination of Nell1-deficient hearts showed heart enlargement and cardiomyopathy, conditions associated with events of myocardial infarction ("MI"). Although the basic vasculature system was observed during embryo development even without a functional Nell1, the amount and complexity (branched network) was significantly reduced in Nell1 mutants. The therapeutic application of Nell1 for heart muscle regeneration is therefore dependent not only on the protein's abilities to signal muscle cell maturation, but also in its capabilities to support the construction of the highly branched vasculature that is required to sustain new heart muscle formation and maintenance of heart function. The inventor also observed that microarray experiments indicate that Nell1 is essential for the proper formation of heart extracellular matrix, main structural components of heart muscle, and proper functioning of genes for heart metabolism and contraction.

Accordingly, the present invention provides methods for treating cardiovascular conditions or disorders by employing a Nell1 protein, functional derivatives thereof, or Nell1 nucleic acid molecules.

The term "condition," as used herein, refers to a disease or ailment. The term "disorder," as used herein, refers to a condition in which there is a disturbance of normal functioning. The term "cardiovascular," as used herein, refers to the heart and/or blood vessels.

Accordingly, the term "cardiovascular condition" or "cardiovascular disorder", as used herein, refers to diseases or aliments that involve the heart, blood vessels (e.g., arteries and veins). Generally, such diseases or aliments result in an abnormality in the cardiac structure, cardiac muscle, and/or cardiac function. The cardiovascular condition or disorder can be acute or chronic.

The term "cardiovascular condition" or "cardiovascular disorder" can be used interchangeably throughout the specification. Examples of a cardiovascular disease include aneurysms, angina, atherosclerosis, cardiomyopathy, congestive heart failure, coronary artery disease, and myocardial infarction, among others. Further examples of cardiovascular conditions include, for instances, blood vessels that have been revascularized. Such patients generally have a stent placed in a blood vessel (e.g., artery, etc.)

A cardiovascular condition especially suitable for being treated with the method of the present invention is myocardial infarction (or "MI"). MI, also known as a "heart attack" or "heart failure", is a medical condition that occurs when the blood supply to a part of the heart is interrupted. MI is often caused by partial or complete occlusion of one or more of the coronary arteries, usually due to rupture of an atherosclerotic plaque. The occlusion of the coronary artery results in cardiac ischemia. The resulting ischemia or oxygen shortage causes damage and potential death of heart tissue.

The term "treating" or "treatment" a disease, as used herein, refers to preventing or delaying the onset of the disease, or when the disease does occur, retard the progression or ameliorate the symptoms of the disease, reduce the extent of tissue injury or damage, or promote recovery of the injured tissue and regeneration of new functional tissue or cells.

The subject suitable for receiving a treatment in accordance with the present invention includes any mammalian subject in need of the treatment. In one embodiment, the subject is a human subject. A subject in need of treatment includes both subjects who have been determined to have a higher risk of developing a cardiovascular disease, and subjects who have a cardiovascular disease, as well as subjects who have recently experienced a cardiovascular event such as MI.

In one embodiment, the method of the present invention is achieved by administration of a Nell1 protein to a subject in need of the treatment.

"A Nell1 protein" as used herein, includes wild type (i.e., naturally occurring) Nell 1 proteins of any mammalian origin, such as human, murine, rat and the like. Preferred Nell1 proteins for use in the present invention include human Nell1 protein (SEQ ID NO: 2), murine Nell1 protein (SEQ ID NO: 4), and rat Nell1 protein (SEQ ID NO: 6).

"A Nell1 protein" as used herein, also includes functional derivatives of a wild type Nell1 protein. A "functional derivative" refers to a modified Nell1 protein which has one or more amino acid substitutions, deletions or insertions as compared to a wild type Nell1 protein, and which retains substantially the activity of a wild type Nell1 protein. By "substantially" is meant at least 50%, at least 75%, or even at least 85% of the activity of a wild type Nell1 protein. According to the present invention, in order for the functional derivative to substantially retain the activity or function of a wild type Nell1 protein, the functional Nell1 derivative shares a sequence identity with the wild type Nell1 protein of at least 75%, at least 85%, at least 95% or even 99%.

The structure of Nell1 proteins has been characterized (see, e.g., Kuroda et al., 1999a; Kuroda et al., 1999b, Desai et al., 2006). For example, the murine Nell1 protein (SEQ ID NO: 4) is a protein of 810 amino acids, having a secretion signal peptide (amino acids #1 to 16), an N-terminal TSP-like module (amino acids #29 to 213), a Laminin G region (amino acids #86 to 210), von Willebrand factor C domains (amino acids #273 to 331 and 699 to 749), and a $Ca^{2+}$-binding EGF-like domains (amino acids #549 to 586).

The secretion signal peptide domain of Nell1 protein is an amino acid sequence in the protein that is generally involved in transport of the protein to cell organelles where it is processed for secretion outside the cell. The N-terminal TSP-like module is generally associated with heparin binding. von Willebrand factor C domains are generally involved with oligomerization of Nell1. Laminin G domains of Nell1 protein are generally involved in adherence of Nell1 protein to specific cell types or other extracellular matrix proteins. The interaction of such domains with their counterparts is generally associated with, for example, processes such as differentiation, adhesion, cell signaling or mediating specific cell-cell interactions in order to promote cell proliferation and differentiation. The $Ca^{2+}$-binding EGF-like domains of Nell1 binds protein kinase C beta, which is typically involved in cell signaling pathways in growth and differentiation.

The amino acid sequence of Nell1 protein is very highly conserved, especially across mammalian species. For example, the murine Nell1 protein shares about 93% sequence identity with the human Nell1 protein (SEQ ID NO: 2), which, in turn, shares about 90% sequence identity with the rat Nell1 protein (SEQ ID NO: 4). Those skilled in the art can use any of the well-known molecular cloning techniques to generate Nell1 derivatives having one or more amino acid substitutions, deletions or insertions, taking into consideration the functional domains (e.g., secretion signal peptide sequence, N-terminal TSP-like module, Laminin G region, von Willebrand factor C domain) of Nell1. See, for example, *Current Protocols in Molecular Cloning* (Ausubel et al., John Wiley & Sons, New York).

The minimum length of a Nell1 functional derivative is typically at least about 10 amino acids residues in length, more typically at least about 20 amino acid residues in length, even more typically at least about 30 amino acid residues in length, and still more typically at least about 40 amino acid residues in length. As stated above, wild type Nell1 protein is approximately about 810 amino acid residues in length. A Nell1 functional derivative can be at most about 810 amino acid residues in length. For example, a Nell1 functional derivative can be at most at most about 820, 805, 800, 790, 780, 750, 600, 650 600, 550, etc. amino acid residues in length.

Once a Nell1 protein derivative is made, such protein can be tested to determine whether such derivative retains substantially the activity or function of a wild type Nell1 protein. For example, the ability of a Nell1 derivative to bind PKC beta can be tested. Suitable assays for assessing the binding of Nell1 to PKC beta is described in e.g., Kuroda et al. (1999b). For example, protein-protein interaction can be analyzed by using the yeast two-hybrid system. Briefly, a modified Nell1 protein can be fused with GAL4 activating domain and the regulatory domain of PKC can be fused with the GAL4 DNA-binding domain. The activity of beta-galactosidase in yeast cells can be detected.

In addition, one can also test the ability of a Nell1 derivative to stimulate differentiation of precursor cells, which are in the cardiomyocyte lineage, towards mature cardiomyocytes. Maturity of cardiomyocytes can be assessed cellularly (histology) and molecularly (expression of cardiac-specific proteins or extracellular matrix materials). Still further, a Nell1 derivative can be tested for its ability to drive osteoblast precursors to mature bone cells, by detecting expression of late molecular bone markers or mineralization (i.e., calcium deposits). By comparing the activity of a Nell1 derivative with that of a wild type Nell1 protein in one or more of the assays such as those described above, one should be able to determine whether such derivative retains substantially the activity or function of a wild type Nell1 protein.

A Nell1 protein or functional derivative thereof may be prepared by methods that are well known in the art. One such method includes isolating or synthesizing DNA encoding the Nell1 protein, and producing the recombinant protein by expressing the DNA, optionally in a recombinant vector, in a suitable host cell, including bacterial, yeast, insect or mammalian cells. Such suitable methods for synthesizing DNA are, for example, described by Caruthers et al. 1985. *Science* 230:281-285 and DNA Structure, Part A: *Synthesis and Physical Analysis of DNA*, Lilley, D. M. J. and Dahlberg, J. E. (Eds.), *Methods Enzymol.*, 211, Academic Press, Inc., New York (1992).

Examples of suitable Nell1 nucleic acid sequences include SEQ ID NOs: 1, 3, and 5. A Nell1 protein or functional derivative may also be made synthetically, i.e. from individual amino acids, or semisynthetically, i.e. from oligopeptide units or a combination of oligopeptide units and individual amino acids. Suitable methods for synthesizing proteins are described by Stuart and Young in "Solid Phase Peptide Synthesis," Second Edition, Pierce Chemical Company (1984), Solid Phase Peptide Synthesis, Methods Enzymol., 289, Academic Press, Inc, New York (1997). Examples of suitable Nell1 amino acid sequences include SEQ ID NOs: 2, 4, 6, and derivatives thereof.

In another embodiment, the method of the present invention is achieved by administration of a nucleic acid molecule encoding a Nell1 protein or functional derivative to a subject in need of the treatment.

Suitable nucleic acid molecules for use in the present invention include nucleic acid molecules having a nucleotide sequence as set forth in SEQ ID NO: 1 (encoding the wild type human Nell1 protein), SEQ ID NO: 3 (encoding the wild type murine Nell1 protein), and SEQ ID NO: 5 (encoding the rat wild type Nell1 protein), as well as degenerate sequences thereof. As used herein, the term "degenerate sequence" refers to a sequence formed by replacing one or more codons in the nucleotide sequence encoding wild type Nell1 protein with degenerate codes which encode the same amino acid residue (e.g., GAU and GAC triplets each encode the amino acid residue Asp).

In some embodiments, nucleic acid molecules for use in the methods of the present invention are provided in an expression vector. Expression vectors for use in the present methods include any appropriate gene therapy vectors, such as nonviral (e.g., plasmid vectors), retroviral, adenoviral, herpes simplex viral, adeno-associated viral, polio viruses and vaccinia vectors. Examples of retroviral vectors include, but are not limited to, Moloney murine leukemia virus (Mo-MuLV), Harvey murine sarcoma virus (HaMuSV), murine mammary tumor virus (MuMTV), and Rous Sarcoma Virus (RSV)-derived recombinant vectors. A Nell1-coding nucleotide sequence can be placed in an operable linkage to a promoter in the expression vector, wherein the promoter directs the expression of the Nell1 protein in the targeted tissue or cells, and includes both a constitutive promoter and a tissue or cell-specific promoter.

A Nell 1 protein, functional derivative thereof or Nell1-encoding nucleic acid molecule can be combined with a pharmaceutically acceptable carrier and prepared in formulations suitable for administration to a subject by injections, implantations, inhalations, ingestions and the like. Pharmaceutically acceptable carriers are described hereinabove and include oils, water, saline solutions, gel, lipids, liposomes, resins, porous matrices, binders, fillers and the like, or combinations thereof. The carrier can be liquid, semi-solid, e.g. pastes, or solid carriers. Except insofar as any conventional media, agent, diluent or carrier is detrimental to the recipient or to the therapeutic effectiveness of the active ingredients contained therein, its use the present invention is appropriate. Examples of carriers include oils, water, saline solutions, gel, lipids, liposomes, resins, porous matrices, binders, fillers, patches, and the like, or combinations thereof. The carrier can also be a controlled release matrix that allows optimum release of a Nell1 protein or nucleic acid admixed therein.

The term "therapeutically effective amount" means the dose required to prevent or delay the onset, slow down the progression or ameliorate the symptoms of the disorder. Precise dosages depend on the disease state or condition being treated and other clinical factors, such as weight and condition of the subject, the subject's response to the therapy, the type of formulations and the route of administration. As a general rule, a suitable dose of a Nell1 composition (i.e., including a Nell1 protein or nucleic acid) for the administration to adult humans ranges from about 0.001 mg to about 20 mg per kilogram of body weight. In some embodiments, a suitable dose of a Nell1 composition for the administration to adult humans is in the range of about 0.01 mg to about 5 mg per kilogram of body weight. However, the precise dosage to be therapeutically effective and non-detrimental can be determined by those skilled in the art.

A Nell1 protein, functional derivative thereof, or nucleic acid molecule can be administered to the subject in any practical and convenient manner. Suitable routes of administration include the oral, nasal, topical, transdermal, and parenteral (e.g., intravenous, intraperitoneal, intradermal, subcutaneous or intramuscular) route. In addition, a Nell1 protein, functional derivative thereof, or nucleic acid molecule can be introduced into the body, by injection or by surgical implantation or attachment, proximate to a preselected tissue or organ site such that the Nell1 material is able to enter the site by direct diffusion. For example, a Nell1 protein, functional derivative thereof, or nucleic acid can be provided in a patch or gel like substances, which, upon administration (by e.g., injection or implantation) can be taken up directly by tissues as a result of diffusing from a site of high concentration to one where there is very low level of the substance. If Nell1 protein, functional derivative thereof, or nucleic acid molecule is administered locally, the formulation is such that the Nell1 protein, functional derivative thereof, or nucleic acid molecule does not diffuse and adversely affect surrounding organs.

Alternatively, a Nell1 protein, or functional derivative thereof, can be administered directly to injured and damaged tissue (e.g., infarct and surrounding border zones). Such administration, can be applied, for example, to treat cardiovascular defects, thus minimizing heart muscle injury or stimulating tissue repair processes in the heart after MI.

Other delivery systems and methods include, but are not limited to: a) catheter-based devices that permit site specific drug delivery to the heart muscle, b) via a thorascopic opening (small minimally invasive wound in the thoracic cavity; similar to laparascopic methods) through which a scope and guided injection device containing Nell1 protein, derivative thereof, or nucleic acid molecule is introduced, c) ultrasonic-based drug delivery methods (see, for example, Mayer et al., *Advanced Drug Delivery Reviews,* 2008, 60:1177-1192 and Bekeredjian et al., *Ultrasound in Medicine and Biology,* 2005, 31:687-691), and d) infusion into the pericardial space (see, for example, Xiao et al., *Am. J Physiol, Heart Circ. Physiol.,* 2008, 294:H12212-12218).

Important general considerations for design of delivery systems and compositions, and for routes of administration, for protein/peptide drugs may apply. For example, the appropriate delivery system for Nell1 protein and/or functional derivatives thereof will depend upon its particular nature, the particular clinical application, and the site of action.

Formulations for oral delivery or systemic delivery, for instance, may require certain considerations due to, for example, instability of Nell1 protein and/or functional derivatives thereof in the gastrointestinal tract, or exposure of Nell1 protein and/or functional derivatives thereof to proteases. Any method known to those skilled in the art can be utilized to address such considerations.

For example, for oral delivery, an absorption-enhancing agent can be utilized. A wide variety of absorption-enhancing agents have been investigated and/or applied in combination with protein compositions for oral delivery and for delivery by other routes (van Hoogdalem, Pharmac. Ther. 44, 407-43, 1989; Davis, J. Pharm. Pharmacol. 44(Suppl. 1), 186-90, 1992). Most commonly, typical enhancers fall into the general categories of (a) chelators, such as EDTA, salicylates, and N-acyl derivatives of collagen, (b) surfactants, such as lauryl sulfate and polyoxyethylene-9-lauryl ether, (c) bile salts, such as glycholate and taurocholate, and derivatives, such as taurodihydrofusidate, (d) fatty acids, such as oleic acid and capric acid, and their derivatives, such as acylcarnitines, monoglycerides, and diglycerides, (e) non-surfactants, such as unsaturated cyclic ureas, (f) saponins, (g) cyclodextrins, and (h) phospholipids.

Alternatively, Nell1 protein and/or functional derivative thereof, can be administered in combination with other drugs or substances that directly inhibit proteases and/or other potential sources of enzymatic degradation of proteins. Yet another alternative approach to prevent or delay gastrointestinal absorption of Nell1 protein and/or functional derivative thereof is to incorporate them into a delivery system that is designed to protect the protein from contact with the proteolytic enzymes in the intestinal lumen and to release the Nell1 protein and/or functional derivatives thereof at the site of cardiovascular injury. A more specific example of this strategy is the use of biodegradable microcapsules or microspheres, both to protect a protein from degradation, as well as to effect a prolonged release of active protein (see, for example, Deasy, in Microencapsulation and Related Processes, Swarbrick, ed., Marcell Dekker, Inc.: New York, 1984, pp. 1-60, 88-89, 208-11).

In a specific embodiment, a Nell1 protein, functional derivative thereof, or nucleic acid molecule is administered to directly repair heart muscle after MI. Delivery can be performed via direct delivery to or near the injured heart muscle site (infarct and border zones) by injection, by catheter, via absorbable biomatrix (i.e. biocompatible porous) material, and the like, and combinations thereof. According to this embodiment, the Nell1 composition is administered to the subject after the initial inflammatory responses subsides—usually within 72 hours, within 48 hours, within 36 hours, within 24 hours, or even within 18 hours of MI, in order to minimize the extent of the injury and achieve better therapeutic efficacy. There is a flood of inflammatory responses immediately after heart muscle injury. It is believed to be optimal to administer Nell1 after this initial defensive response of the surrounding tissue. Regenerative processes, which naturally begins after the inflammatory response slows down, are where Nell1 is likely to work best.

Further according to the present invention, a Nell1 protein, functional derivative thereof, or Nell1-encoding nucleic acid molecule can be used independently or in conjunction with additional therapeutic compositions useful for treating a cardiovascular condition.

In a specific embodiment, a Nell1 protein, functional derivative thereof, or Nell1-encoding nucleic acid molecule is used together with stem cells for the repair and regeneration of damaged cardiac muscles and blood vessels.

Cell-based therapies for the repair and regeneration of damaged cardiac muscles and blood vessels utilize implantation of cells (such as cardiomyocytes), or introduction of stem cells isolated from adult bone marrow to develop new cardiac muscle in the area of implantation. See, e.g., Orlic et al., 2001; Rubart et al., 2006; Ott et al., 2006; Rosenthal et al., 2006. Without being bound by theory, the use of Nell1 increases the efficiency of cell-based therapies for the repair and regeneration of damaged cardiac muscles and blood vessels.

According to the present invention, a Nell1 protein or nucleic acid molecule can be co-delivered with the appropriate cells, e.g., cardiomyocytes or adult stem cells, directly to the damaged sites of a subject using biological matrices or direct injection methods already in practice for cell-based therapies.

In another embodiment, a Nell1 protein, functional derivative thereof, or Nell1-encoding nucleic acid molecule is used in vitro to stimulate or promote the development and differentiation of stem cells into cardiomyocytes useful for the repair and regeneration of damaged cardiac muscles and blood vessels. See, for instance, example 7.

This invention is further illustrated by the following examples, which are not to be construed in any way as imposing limitations upon the scope thereof. The terms and expressions which have been employed in the present disclosure are used as terms of description and not of limitation, and there is no intention in the use of such terms and expressions of excluding any equivalents of the features shown and described or portions thereof. It is to be understood that various modifications are considered to be included within the scope of the invention. All the publications mentioned in the present disclosure are incorporated herein by reference.

EXAMPLE 1

Nell1$^{6R}$ Mutant Mouse

The Nell1$^{6R}$ mutant mouse was used in the experiments described in the following examples. Generation, breeding and maintenance of this mutant mouse is described in U.S. Published Application 2006/0053503, which is incorporated herein by reference. Briefly, the mutant mouse contains a recessive neonatal-lethal point mutation in the Nell1 gene, originally induced by N-ethyl-N-nitrosourea (ENU). Nell1$^{6R}$ has T to A base change that converts a codon for cysteine into a premature stop codon (TGT to TGA; Cys(502)Ter), resulting in a severe truncation of the Nell1 protein product and a marked reduction in steady state levels of the Nell1 transcript.

EXAMPLE 2

Heart Defects in Nell1$^{6R}$ Mutant Mouse

Formalin-fixed specimens were analyzed by heart length and width measurements. These measurements were completed on wild type, heterozygous, and mutant mice at the 18.5-day embryonic stage. Further observations were made using standard histological methods (haematoxylin and eosin staining on mouse sagittal sections).

Nell1$^{6R}$ mice were observed to have significantly enlarged hearts based on length and width measurements. As shown in Table 1, length measurements for all three genotypes did not differ significantly. However, based on the statistical T-test, the width measurements for mutant mice was significantly greater compared to the width for wild type and heterozygous mice, this confirming presence of an abnormal heart phenotype in mutant mice.

Figures 2A, 2B:
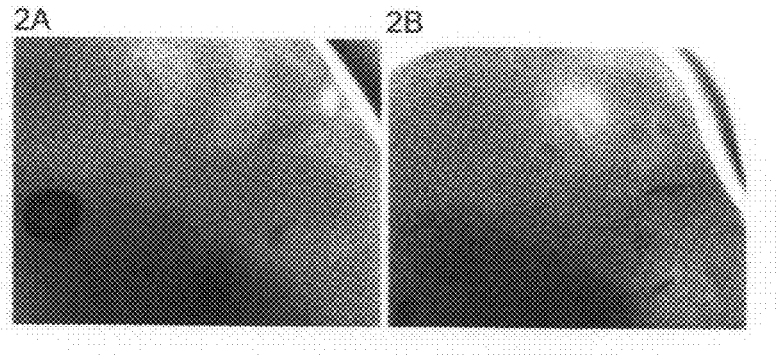
FIGS. 2A-2B (in color) demonstrate that Nell1 protein is required for blood vessel formation and establishment of a complex vascular network. The loss of Nell1 function resulted in a significant reduction of the number of blood vessels and extensive branching of the vasculature in Nell1$^{6R}$ mutants (FIG. 2B) compared to (FIG. 2A) normal fetuses. The decrease in blood vessel formation was observed throughout the fetal body.

Examination of the haematoxylin and eosin-stained slides showed dramatically reduced blood flow out of the heart. As shown in FIGS. 1-2, wild-type and heterozygote mice showed arteries filled with blood whereas blood was not a very prominent feature in slides of mutant mice. Therefore, the loss of Nell1 function resulted in a significant reduction of the number of blood vessels and extensive branching of the vasculature in mutants as compared to wild type fetuses. The decrease in blood vessel formation was observed throughout the fetal body.

Figures 3A, 3B:
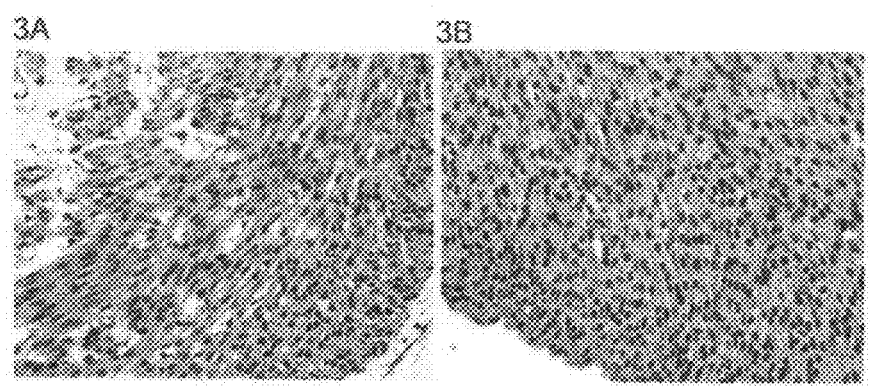
FIGS. 3A-3B illustrate severe cardiovascular defects and neonatal lethality associated with the complete loss of Nell1 function in the mouse. The cardiovascular defects resulting from the complete loss of Nell1 function in Nell1$^{6R}$ was associated with decreased blood circulation into the heart muscles and predominance of increased numbers of immature cardiomyocytes. The dense packing of smaller cardiomyocytes in the mutant (FIG. 3B) was very apparent in the denser/darker staining with haematoxylin and eosin, compared to the wild type (FIG. 3A). These cardiovascular defects are evident in E18.5 day fetuses recovered by caesarean.
Figures 4A, 4B, 4C:
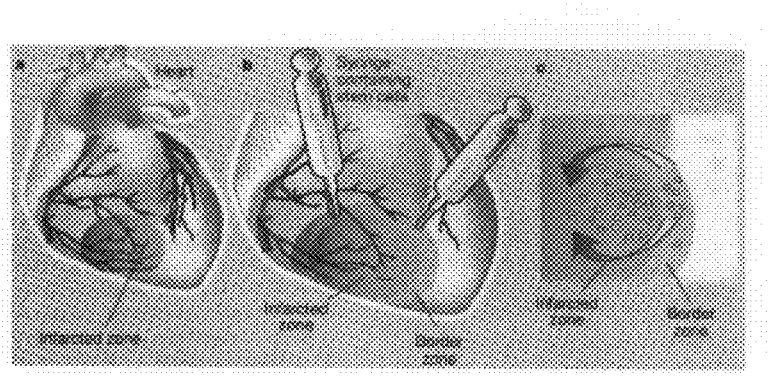
FIGS. 4A-4C illustrate a strategy for treatment of heart muscle injury after MI in rodents using direct injection of stem cells or drugs to the border zone.
Figures 6A, 6B, 6C, 6D:
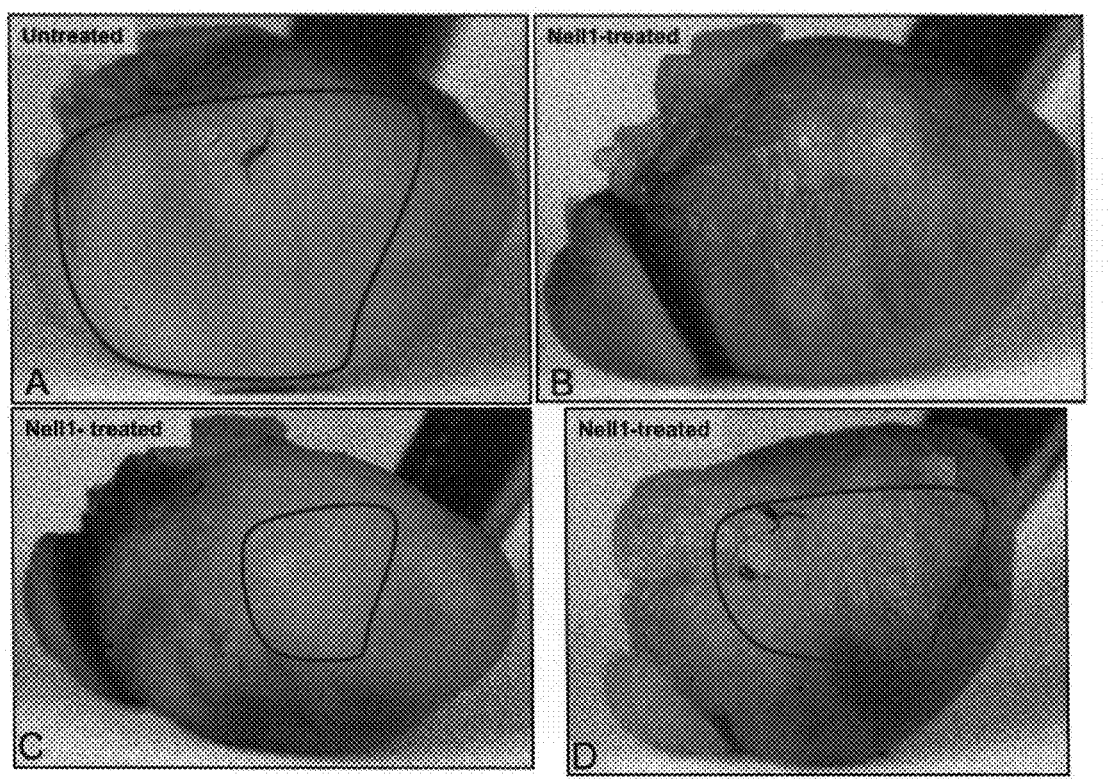
FIGS. 6A-6D. NELL1 Protein Treatment of Damaged Heart Tissue in Mice with Myocardial Infarction (MI). (6A) Untreated mouse hearts with MI due to the loss of blood supply from a ligation of the left anterior descending coronary artery had a readily visible creamy white looking damaged tissue on the surface of the heart (17 days post MI-induction). All Nell1 protein treated hearts had lesser amount of damaged tissue as illustrated in FIG. 7B to 7D. The damaged sections (outlined by blue lines) in controls were typically at least 50% while the treated hearts had barely visible (6B) to as high as 30% infarcts observed (6D).
Figures 7A, 7B, 7C, 7D, 7E, 7F:
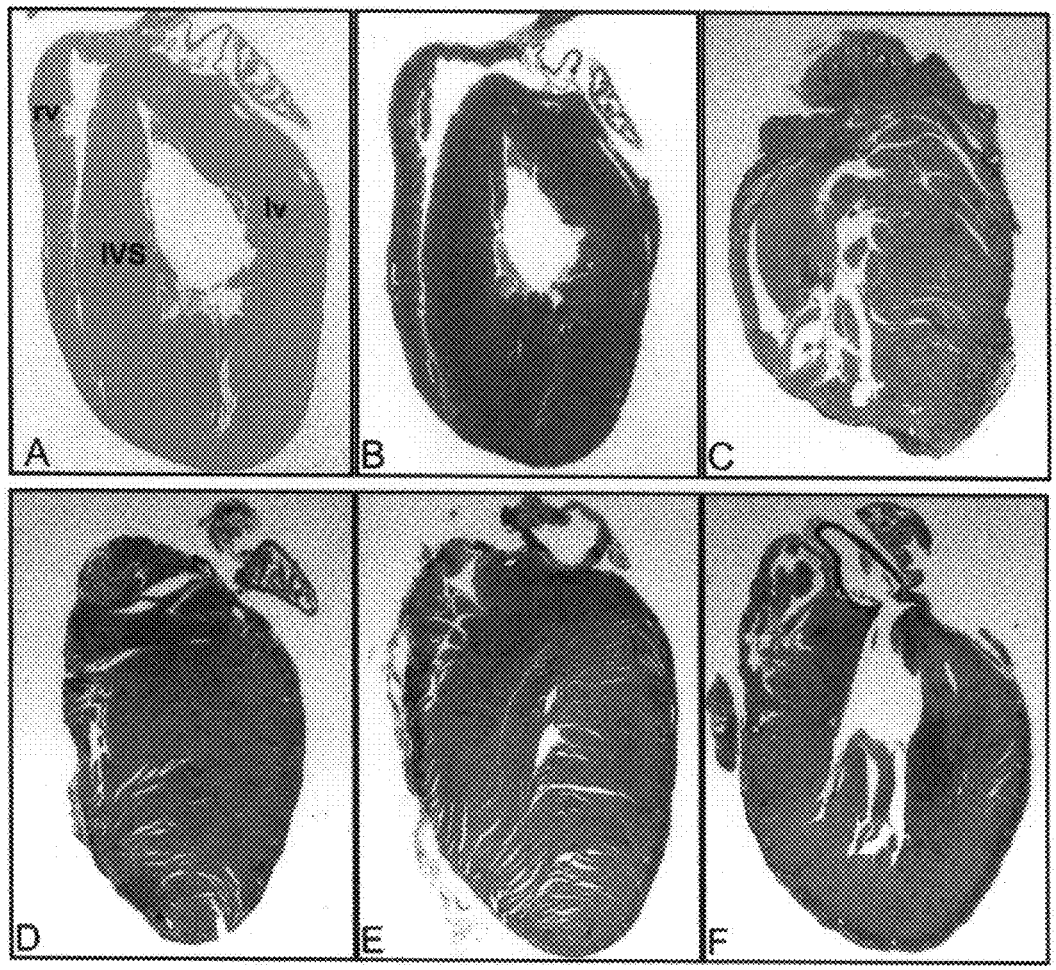
FIGS. 7A-7F. Reduction of Damaged Heart Tissue Incurred From Myocardial Infarction in Nell1-treated Hearts. Longitudinal sections of normal hearts stained with either haematoxylin and eosin (7A) or masson-trichome (7B) show intense staining of the heart muscle and reveals a very compact organization of the muscle tissues in the right and left ventricles (rv and lv respectively), and the interventricular septum separating the two ventricular chambers (IVS). After a myocardial infarction event, the muscle tissues died due to a lack of oxygenated blood supply and the deterioration of the muscle architecture was evident by the large gaps in the tissue and the decreased intensity of the staining (7C; 17 days post-MI). Hearts with MI that were treated with the Nell1 protein had lesser damage in the heart tissue from the surface to just before the middle of the heart (7D and 7E). In some hearts the improvement was manifested even deeper into the middle section of the heart (7F).

In addition, a larger number of immature heart cells and lesser extracellular matrix were observed in mutant mice as compared to wild type mice (FIG. 3A-3B). The dense packing of smaller cardiomyocytes in the mutant (FIG. 3B) was very apparent in the denser/darker staining with haematoxylin and eosin, compared to the wild type (FIG. 3A).

TABLE 1

Measurements of Nell1$^{6R}$ Hearts Indicating Heart Enlargement
Measurement (mm) of E18.5 fetal heart width and length of Nell1$^{6R}$ heterozygote and homozygote mutant mice compared with wild-type littermates. There is significant enlargement of fetal hearts in homozygote mutant compared to the heterozygotes and normal mice.

|  | Homozygote Nell16R/Nell 16R | Heteozygote +/Nell 1 6R | Wild-type +/+ |
|---|---|---|---|
| Width | 3.3 | 2.8 | 2.7 |
|  | 2.5 | 2.8 | 2.8 |
|  | 2.8 | 2.3 | 2.8 |
|  | 2.3 | 2.7 | 2.5 |
|  | 2.8 | 2.8 | 2.7 |
|  | 3.0 | 2.5 | 2.3 |
|  | 3.2 | 2.5 | 2.2 |
|  | 3.0 | 2.5 | 2.5 |
|  | 2.8 | 2.2 | 2.8 |
|  | 2.8 | 2.5 | 2.7 |
|  | 3.3 | 2.2 | 2.7 |
|  | 3.0 | — | 2.2 |
|  | 3.0 | — | 2.5 |
|  | 2.5 | — | 2.3 |
|  | 2.5 | — | — |
|  | 3.0 | — | — |
|  | 2.5 | — | — |
| No. of Fetuses | 17 | 11 | 14 |
| Average | 2.853 | 2.530 | 2.476 |
| Length | 3.2 | 3.7 | 2.7 |
|  | 2.8 | 3.2 | 2.7 |
|  | 2.8 | 2.8 | 3.3 |
|  | 2.7 | 3.2 | 3.0 |

TABLE 1-continued

Measurements of Nell1[6R] Hearts Indicating Heart Enlargement
Measurement (mm) of E18.5 fetal heart width and length of Nell1[6R]
heterozygote and homozygote mutant mice compared with wild-type
littermates. There is significant enlargement of fetal hearts in
homozygote mutant compared to the heterozygotes and normal mice.

|  |  |  |
|---|---|---|
| 3.0 | 3.2 | 3.3 |
| 3.2 | 3.0 | 3.0 |
| 3.2 | 3.0 | 2.5 |
| 3.3 | 3.3 | 3.0 |
| 3.0 | 2.8 | 3.3 |
| 2.8 | 3.0 | 3.2 |
| 3.2 | 2.8 | 3.3 |
| 3.2 | — | 2.7 |
| 3.2 | — | 2.8 |
| 2.8 | — | 3.0 |
| 2.5 | — | — |
| 3.0 | — | — |
| 2.8 | — | — |
| No. of Fetuses 17 | 11 | 14 |
| Average 2.984 | 3.091 | 2.988 |

T-Test p-values

| | Mutant: Wild-type | Mutant: Heterozygote | Heterozygote: Wild-type |
|---|---|---|---|
| Width | 0.0012442891 | 0.0046893426 | 0.6143698331 |
| Length | 0.9351530349 | 0.2470911230 | 0.3514701862 |

These above cardiovascular defects were evident in E18.5 day fetuses recovered by caesarean. Additionally, wild type and heterozygote mice had spongy lungs that filled their entire thoracic cavity, while mutant mice had compact, dense lungs. Mutant mice did not survive birth. The severity of the heart and blood vessel defects were likely to be the cause of the death of the fetuses during the birth process reported earlier (Desai et al, 2006). Fetuses that were recovered by caesarean were unable to breathe as depicted in the collapsed lung in the mutants.

EXAMPLE 3

ECM Genes Affected by Nell Influence Heart Development

A comprehensive gene expression analysis using public database (UCSC Genome Browser, Mouse Genome Informatics, Integrated Cartilage Gene Database, PubMed) was conducted to investigate the relationship between cardiovascular development and each of the 28 extracellular matrix (ECM) genes which were shown previously (Desai et al., 2006) to exhibit reduced expression in Nell1[6R] mutant mouse bodies. Of the 28 ECM genes studied, the bioinformatics analysis showed that the majority of genes with reduced expression in Nell-1 deficient mice are normally expressed in the heart (79% of the analyzed ECM genes; 22/28), blood vessels (71%; 20/28) and bone marrow (61%; 17/28) (See Table 2). The Mouse Genome Informatics database referenced several genes (Col15a1, Osf-2, Bmpr1a, Pkd1, Mfge8, Ptger4, Notch3) that have been mutated in mice and actually manifest abnormalities in cardiovascular development.

Mouse mutations in some of these genes display heart deformities commonly associated with heart enlargement, as shown in Table 3 below.

TABLE 2

Expression profile of genes in the Nell1 pathway and association with mutant mouse phenotypes.

| Gene Symbol | Gene Name | Expression heart | vascular | blood | bone marrow | # abnormal heart phenotype[13] | # total mutants[13] |
|---|---|---|---|---|---|---|---|
| Tnxb | tenascin | 10 | 10 | 11 | 11 | | 2 |
| Prg4 | proteoglycan 4 | 33 | 12 | 12 | | | 1 |
| Thbs3 | thrombospondin 3 | 10 | 10 | 12 | | | 2 |
| Col5a3 | collagen 5 alpha 3 subunit | | | | | | |
| Neurog2 | neurogenin 2 | | | | | | 5 |
| Col5a1 | procollagen type V, alpha 1 | 10 | 10 | 10 | 10 | 1 | 1 |
| Col6a1 | procollagen Type VI aloha 1 | 10 | 16 | 12 | 10 | | 1 |
| Col15a1 | procollagen type XV, alpha 1 | 10 | 19 | 10 | 12 | 1 | 1 |
| Pacsin3 | PKC and casein kinase substrate in neurons 3 | 10 | | | 10 | | |
| Tnc | tenascin c | 10 | 10 | 21 | 11 | | 3 |
| Col12a1 | procollagen type XII, alpha 1 | 10 | 12 | | 10 | | |
| Chad | chondroadherin | 16 | 16 | | | | |
| Osf2-pending | osteoblast specific factor 2 | 10 | 10 | | 10 | 1 | 2 |
| Col17a1 | procollagen type XVII alpha 1 | | | | | | |
| Prkcc | protein kinase C | | | | | | 2 |
| Prkch | protein kinase C, eta symbol | 10 | 10 | 10 | 10 | | 1 |
| Bk-pending | brain and kidney protein | | | | | | |
| Ptk9l | PTK9L protein tyrosine kinase 9-like | 10 | 10 | 10 | 10 | | |
| Npdc1 | neural proliferation, differentiation and control gene | 10 | 10 | | | | 1 |
| Bmpr1a | bone morphogenetic protein receptor type 1a | 10 | 12 | | 10 | 2 | 4 |
| Pkd1 | polycystic kidney disease I homolog | 10 | 27 | 10 | 12 | 7 | 12 |

TABLE 2-continued

Expression profile of genes in the Nell1 pathway and association with mutant mouse phenotypes.

| Gene Symbol | Gene Name | Expression heart | vascular | blood | bone marrow | # abnormal heart phenotype[13] | # total mutants[13] |
|---|---|---|---|---|---|---|---|
| Tnfrsf11b | tumor necrosis factor (ligand) | 10 | 34 | | 12 | | 3 |
| Mfge8 | milk fat globule-EGF factor 8 protein | 10 | 12 | 10 | 10 | 1 | 5 |
| Matn3 | matrilin 3, cartilage matrix protein | 28 | | | | | 1 |
| Bmp7 | bone morphogenetic protein type 7 | 10 | | | 10 | | 8 |
| Matn2 | matrilin 2, cartilage matrix protein 2 | 10 | 10 | 10 | 10 | | 2 |
| Ptger4 | prostaglandin E receptor 4 | | 10 | 10 | 10 | 3 | 4 |
| Notch3 | notch gene homolog 3 | 10 | 30 | | | | 4 |
| | # of Genes | 22 | 20 | 13 | 17 | 7 | 20 |
| | Percentage | 79% | 71% | 46% | 61% | 25% | 71% |

TABLE 3

Mutated genes causing heart defects associated with enlargement

| Gene | Defect |
|---|---|
| Col6a1 | Dilated descending aorta |
| Bmpr1a | Persistent truncus arteriosus |
| | Outflow tract formation abnormalities |
| Pkd1 | Vascular leaks/ruptures |
| | Endocardial cushion defects |
| | Abnormal atrial septum morphology |
| | Double outlet right ventricle |
| | Abnormal septation |
| Bmp7 | Lack of endocardial cushion formation |
| Ptger4 | Dilated left ventricle |
| | Patent ductus arteriosus |
| | Congestive heart failure |

EXAMPLE 4

Gene Expression in Nell1[6R] Mutant Mouse

To define the involvement of Nell1 in the known molecular pathways that govern heart structure and function, a comprehensive gene expression analysis was conducted in the entire mouse genome (~30,000 genes) of normal fetal hearts and those dissected from Nell1[6R]. This analysis consisted of 50 mutant fetal hearts separated into 4 pools of 10-13 hearts and 35 normal hearts separated into three pools of 10-12 hearts (18.5 days of gestation). RNAs were extracted from the pooled tissues, processed for microarray analysis on the Illumina Mouse V6 chips and scanned with Illumina Beadstation 500GX. Data was analyzed with the BeadStudio software and Gene Ontology Tree machine. At least 345 genes were identified that were differentially expressed between normal and mutant samples (at p value=0.001 for the microarray detection and differential p values; denotes a very high statistical significance). Table 4 lists a representative sampling of genes influenced by Nell1 that already have established functions in cardiovascular conditions. Table 4 also provides the literature references for the specific studies that have demonstrated these gene functions.

Table 4 shows a number of genes in the Nell1 pathway that have been implicated in the processes that ensue after heart failure. The ability of Nell1 to stimulate proteins that control cell differentiation and proper secretion of the cardiac ECM strongly suggests that this protein can restore proper ECM constitution and orientation in heart muscle after a heart attack, thereby preventing or alleviating heart muscle damage and subsequent loss of heart function (or death) resulting from MI.

EXAMPLE 5

The data presented here were based on studies of the Nell1[6R] mutant mouse. Rodent Nell1 studies are believed to translate accurately to the human situation. The complete mouse Nell1 coding sequence has been reported (Genbank Accession No. AY622226; Desai et al., 2006). A comparison of this sequence with the most current human Nell1 gene in the public genome databases (UCSC Genome Browser and NCBI) indicates a very high homology of 87% gene sequence identity. The corresponding 810-amino acid residue polypeptides have a 93% identity in their amino acid sequences (FIG. 5). When one considers conservative substitution of similar amino acids, the human and mouse Nell1 proteins are 97% conserved. This remarkable degree of gene and protein structure conservation suggests the conservation of functions and fundamental mechanisms of Nell1-mediated pathways in human and mouse.

EXAMPLE 6

Animal Model for Assessing Therapeutic Efficacy of Nell1 for MI

The efficacy of the Nell1 protein for regenerating cardiac muscle after damage induced by a myocardial infarction (MI) is tested in a widely used and accepted in vivo animal model. Myocardial infarction is induced in a murine in vivo model by blocking the main blood supply line to the left ventricle. The surgical procedures for generating this model are described in detail by several publications (Patten et al., 1998; Tarnavski et al., 2004; Ahn et al., 2004).

Briefly, mice are anesthetized, restrained in a supine position, and intubated with pure oxygen regulated by a small animal ventilator. A thoracotomy is performed under a dissecting scope, at the fourth or fifth intercostal space of the left side, between the heart and lung margins. The thoracic surgical hole is enlarged using retractors and the pericardial sac is gently torn with fine forceps.

The left anterior descending coronary artery (LAD) is visualized and ligated by passing a tapered microsurgical needle (¼ circle, 140 microns) with a black silk monofilament suture (size 7 or 8) underneath the coronary artery and tying the suture to completely stop the blood flow in the artery. A small polyethylene tubing (PE 10) 2-3 mm is placed between the tie and the LD to minimize cutting and severely injuring the artery.

Myocardial infarction is confirmed by observing for blanched or white appearance of the left vertical that correspond to the muscles that have lost blood supply and the alteration of the wave pattern (pronounced ST wave elevation) in an electrocardiogram. Since the LAD provides the blood supply to the left ventricle, this surgically-induced myocardial infarction will cause the death of myocardial tissue (necrosis) in the left ventricular wall and the anterior section of the interventricular section. The size of the myocardial infarction lesions/infarcts can be controlled by the exact position of the ligation along the LAD. Ligation at a high position (atrioventricular junction) will reduce blood flow to a larger area and make larger infarcts while ligations at lower areas will make medium or small lesions. Ligature position is kept constant for any given experimental group to keep the infarction size constate.

After myocardial infarction induction, the thoracic and skin wounds are sutured and mice are allowed to recover from anesthesia on a heating pad or with heat lamps.

To test the ability of Nell1 to repair cardiac tissue damage due to an acute myocardial infarction event, purified Nell1 protein are delivered directly into the surrounding tissue around the visible infarct and within the infarct. Direct delivery of Nell1 protein is performed by reopening the original thoracic wound used to induce the infarct.

Nell1 and functional derivatives thereof containing EGF like domains and/or the von Willebrand like domain of Nell1 are administered at 2-3 points along one side of the infarct border zone. In some animals, direct delivery of Nell1 protein is administered via microinjection, application of Nell1 in a gel or microspray, via nanoparticles, or time-release patches. In others, it is administered via a Nell1 protein expression vector (continuous delivery). Administration of Nell1 is performed after the initial surge of inflammatory response triggered by cardiac damage and at the time heart tissue attempts innate regenerative mechanisms (approximately 4-5 hrs after MI). The effects of Nell1 administration are evaluated by standard histology and immunohistochemistry techniques for detection of proteins associated with cardiac tissue regeneration (Orlic et al., 2001).

EXAMPLE 7

In Vitro Stem Cell Therapy

A promising approach in the field of heart muscle regeneration after MI is the introduction of either embryonic or adult mesenchymal stem cells into the damaged heart. However, data indicate that although new heart muscle cells can be regenerated that the new tissue may not necessarily display the full functional capacity of mature heart tissue (contractility).

To promote full functional capacity of mature heart tissue, Nell 1 protein and functional derivatives thereof containing EGF like domains and/or the von Willebrand like domain of Nell1 are co-delivered with stem cells to the injured heart muscle using the same strategies currently in use for stem cell delivery.

EXAMPLE 8

Animal Model for Assessing Therapeutic Efficacy of Nell1 for Myocardial Ischemia and Reperfusion Injury The efficacy of the Nell1 for regenerating cardiac muscle after damage induced by myocardial ischemia and reperfusion injury is tested in a widely used and accepted in vivo animal model. Myocardial ischemia and reperfusion injury is induced in an in vivo murine model as follow:

1. After anesthesia, intubation and hook-up to a mouse ECG machine, the chest cavity of the mouse is opened at the intercostal space (usually $4^{th}$ or $5^{th}$) and the opening is retracted to reveal the left side of the heart and to locate the LAD artery. The pericardial sac is torn gently with forceps and the LAD is positioned for easy access. All surgical steps are done under a dissecting microscope.
2. A tapered needle (¼ circle 140 microns) with a size 8 silk or monofilament suture is partially passed underneath the artery. A small tubing 1-1.5" in length (e.g. polyethylene size 10 tubing) is placed on top and parallel to the LAD artery and perpendicular to the length of the needle. The suture is then pulled and a surgical tie is made such that the tubing is tied with the artery located beneath it.
3. The interruption of blood flow to the left ventricular heart muscles is easily visualized by a blanched or white appearance of the affected region (where infarct develops). The ECG will confirm the ischemia by the alteration of the wave pattern (e.g. ST segment elevation, T wave anomalies) compared to the normal pattern. The change indicates that the LAD is successfully ligated and restricted blood flow to the left ventricle has functionally induced an ischemic event.
4. The chest cavity and the skin are sutured such that one end of the tubing is sticking out of the thoracic area above the sutured skin. After the desired amount of time of ischemia, the tubing is gently pulled out to relax the knot/ligated suture thereby allowing reperfusion of blood into the affected area.
5. Reperfusion is indicated by the return of the ECG pattern to normal or near normal pattern. Different groups of mice with varying times of occlusion before reperfusion are made.
6. Varying concentrations of Nell1 protein are administered via intraperitoneal injection or using a catheter device that is placed before the chest cavity is closed after LAD ligation and ischemia. The catheter device allows for controlled delivery so that Nell1 protein can be delivered immediately after reperfusion or given time points after reperfusion is induced. In other models, Nell 1 protein is administered by reopening the surgical sutures and re-entry to the chest cavity and direct Nell1 delivery by microinjection or gel patch.

EXAMPLE 9

Animal Model for Assessing Therapeutic Efficacy of Nell1 for Cardiac Hypertrophy The use of Nell1 protein as a therapeutic for cardiac hypertrophy is tested in a widely used and accepted in vivo animal model. Cardiac hypertrophy is generated by physical/surgical means [pressure-overload].

In the in vivo pressure overload animal model, the aorta of a mouse/rat or large animal is banded to reduce the diameter and thus the blood in the left ventricle builds up pressure and induces hypertrophy of the left ventricle (Tarnavski et al 2004). This type of animal model mimics the human condition of aortic stenosis where the narrowing of the aortic valve restricts blood flow from the left ventricle to the aorta. The persistent increased pressure in the left ventricle leads to increase in muscle mass (hypertrophy) of the walls. This model is generated as follows:

1. Mice are anesthesized and a 5 mm transverse incision is made at the level of the left armpit, 2 mm away from the sternal border. A small incision (5 mm) is made at the $2^{nd}$ intercostal space and opened with microretractors.
2. The thymus and fat covering the aortic area are pushed away and the pericardial sac is gently torn. The ascending portion of the aorta is located and bluntly dissected from the pulmonary trunk and forceps is placed underneath the ascending aorta
3. A 7-0 silk suture is placed around the aorta and a loose knot is made. A 25 or 27 gauge needle (outer diameter of 0.51 mm) that is bent into an L shape is placed through the loose loop, positioned above and parallel to the aorta and a second knot is tied securely. The needle is retracted to yield a constricted aorta (60-80% constriction for a 27 gauge). Two more knots are tied.
4. The chest cavity is closed by suturing ribs and then the skin wound.

Nell1 protein and functional derivatives thereof containing EGF like domains and/or the von Willebrand like domain of Nell1 are administered as an injectable after the onset of hypertrophic changes and heart function anomalies detected by ECG. Times of administration are tested as one high dose after hypertrophy is diagnosed or at lower doses given multiple times (weekly) after hypertrophy is diagnosed. Efficacy of the treatment is evaluated by quantitative measurements of ventricular and heart size, physiological monitoring by ECG and other heart visualization tools, molecular markers for heart failure etc. as described earlier.

EXAMPLE 10

Animal Model for Assessing Therapeutic Efficacy of Nell1 for Cardiomyopathy

The use of Nell1 protein as a therapeutic for cardiomyopathy is tested in a widely used and accepted in vivo animal model. The in vivo mouse model of cardiomyopathy is generated by gene-targeted approaches such as knock-outs or over-expression of a single gene, wherein the homozygotes (two mutant gene copies) and/or heterozygotes (one mutant copy) can survive to the juvenile or adult stage. Suitable in vivo mouse models of cardiomyopathy contain knock-outs or over-expression of genes and pathways (e.g., (extracellular matrix and matricellular proteins, tenascins, thrombospondins, matrilins, etc.) that are controlled by the Nell1 signaling protein. A specific example of an appropriate small animal model is the targeted knockout of the mouse Nov (Ccn3) gene reported by Heath et al. (*BMC Developmental Biology* 2008: 8:18).

Briefly, Nov (Ccn3) mutant mice are generated. Imaging of hearts by echocardiograms and electrocardiograms are conducted to determine heart function and presence of visible heart structure anomalies prior to treatment.

Nell1 protein and functional derivatives thereof containing EGF like domains and/or the von Willebrand like domain of Nell1 are administered by intraperitoneal injection to young Nov (Ccn3) mutant mice and corresponding controls during the first two months of life. Various dosages and timing regimens are tested. After treatment, heart function parameters are measured in Nell1-treated and controls during the time that untreated mutant mice show the severe symptoms of cardiomyopathy, generally at 4-5 months in Nov mice.

After cardiovascular functional/physiological studies, the mice are sacrificed and hearts are dissected and fixed for morphological and histological evaluation such as: total heart size, chamber sizes (especially left ventricle), heart valve structure, chordae tendinae, interventricular septum, heart muscle cell (cardiomyocyte) size and appearance, vessels going in and out of the heart etc.

EXAMPLE 11

NELL1 Protein Treatment of Heart Muscle Damage from Myocardial Infarction

The ability of Nell1 protein to trigger cellular pathway(s) for regeneration of damaged heart muscle was demonstrated in an in vivo mouse model. A heart attack or myocardial infarction was generated in 4-5 month old adult mice (strain C57Bl/6J) by surgically tying the left anterior descending (LAD) coronary artery, which is the main blood supply line to the left ventricle (lv) and the interventricular septum (IVS). The left ventricle pumps oxygenated blood through the aorta into the rest of the body while the IVS divides the right and left ventricles of the heart. LAD ligation in animal models results in the damage and subsequent death of the heart muscle tissue. Table 5 summarizes the results of treating mouse hearts with the purified human NELL1 protein on the third day post-MI event. The NELL1 protein was diluted in phosphate buffered saline (PBS) and was delivered directly onto the damaged heart muscle as a very concentrated microdrop, while the mice were under anaesthesia and intubation for about an hour. Three mice were treated with 312 ng and four mice with 624 ng purified NELL1 protein. Four mice underwent the same cardiac surgery but were given a microdrop of PBS on the damaged heart tissue and served as controls. In addition to these controls, over 20 MI mice were previously generated and studied to obtain consistency in MI surgical and post-surgical techniques. These earlier "controls" displayed the same characteristics as controls represented in Table 5. All treated and untreated mice were maintained for an additional 14 days before they were sacrificed to collect hearts and other major organs (a total of 17 days post-MI). Heart size measurements indicated slight increases in both heart width and depth in Nell1-treated hearts. Remarkably ALL treated mice showed dramatically lesser visible areas of the infarcted tissue on the surface of the heart. In 6 out of 7 hearts the damaged tissue was only visible under the microscope after they were fixed in buffered formalin. FIG. 6A-6D show the range of improvement observed in NELL1-treated hearts, from barely visible to about 30% infarct sizes in comparison to the usual 50-90% infarct sizes seen in controls. FIG. 7A-7D present histological analysis of sectioned hearts stained with Masson-Trichome and further confirmed that there is decreased damage at the cellular level in the NELL1-treated hearts compared to the controls. At 17 days post-MI, heart muscle tissue is severely damaged such that huge gaps appear within the untreated heart muscle in the left ventricle to the interventricular septum. In contrast, there is a consistent and dramatic reduction in the amount of breakdown or damage observed in the heart muscle of treated mice. These data from an in vivo MI mouse model illustrates that clinical approaches that will enable delivery of Nell1 protein directly onto damaged heart muscle will be effective in reducing the effects of an MI event.

TABLE 4

GENES IN NELL1 PATHWAY ASSOCIATED WITH KNOWN CARDIOVASCULAR DISORDERS

| GENE and DESCRIPTION | UP (↑) OR DOWN (↓) REGULATION [p value ≤0.001] | ASSOCIATION WITH HEART DISORDERS AND DISEASES | REFERENCES |
|---|---|---|---|
| Tpm2; tropomyosin 2, beta | ↑4.3 | Cardiac-specific myofibrillogenesis; Cardiomyopathy | Denz et al., 2004 |
| Dmn; desmuslin transcript variant 1 | ↑9.4 | Hypertrophic Cardiomyopathy; heart failure | Mizuno et al., 2001 |
| Acta1; skeletal muscle actin alpha 1 | ↑2.8 | Hypertrophic cardiomyopathy; heart failure | Lim et al., 2001 |
| Tpm1 tropomyosin alpha 1 | ↑4.8 | Hypertrophic cardiomyopathy; heart failure | Wernicke et al., 2007; Kostin et al., 2007 |
| Lgals3; lectin, Galactose binding, soluble 3 | ↑2.6 | Acute heart failure biomarker; excellent predictor of mortality within 60 days; increases in failure prone hypertrophied hearts; aortic stenosis; induces cardiac fibroblast proliferation, collagen deposition | Van Kimmenade et al., 2006; Sharma et al., 2004 |
| Spp1 Secreted phosphoprotein 1 (osteopontin) | ↑2.3 | Heart contractility via control of ECM proteins Inflammation control in hypertrophy, myocardial infarction and heart failure, valvular stenosis | Okamoto, 2007 Singh et al., 2007 |
| Fhl1 Four and a half limb domains | ↑1.3 | Atrial fibrillation in cardiac arrhythmia; β-adrenergic induced cardiomypathy and heart failure (β-blocker pathway); cardiac remodeling by transcriptional regulation and myofilament assembly | Chen et al., 2007 Lim et al., 2001 |
| Aqp1; aquaporin 1 | ↑1.3 | Myocardial edema | Egan et al., 2006 |
| Il6st Interleukin 6 signal transducer | ↑1.5 | Cardiac hypertrophy | Terrell et al., 2006 Coles et al., 2007 |
| Tnc Tenascin c | ↓1.5 | Inflammation induced tissue remodeling in acute myocardial infarction, acute myocarditis and cardiomyopathy, left ventricular remodeling | Terasaki et al., 2007 |
| Tnxb Tenascin xb | ↓1.8 | Cardiac nerve sprouting after MI contributing to arrhythmia and sudden cardiac death | Lai et al., 2000 |
| Igfbp5 Insulin growth factor binding protein 5 | ↓1.3 | Atrophy; Adaptive cardiac hypertrophy | Baurand et al., 2007 |
| Fgl2 Fibrinogen-like protein | ↓1.4 | Acute congestive heart failure without structural abnormalities; contractile dysfunction and rhythm abnormalities | Mu et al., 2007 |
| Ctgf; connective tissue growth factor | ↓1.3 | Excessive myocardial fibrosis and diastolic heart failure | Koitabashi et al., 2007 |
| Dpt; dermatopontin | ↓1.5 | ECM remodeling in myocardial infarction | Takemoto et al., 2002 |
| Ldlr; low density lipoprotein receptor | ↓1.5 | Heart failure | Weiss et al., 2006 |
| Nppb Natriuretic peptide precursor type b | ↓1.3 | Cardiac fibrosis Congestive heart failure and myocardial infarction Biomarker for heart failure | Tamura et al., 2000 Hejmdal et al., 2007 Seferian et al., 2007 Doust et al., 2004 |
| Nppa Natriuretic peptide precursor type a | ↓1.5 | Cardiac fibrosis Congestive heart failure and myocardial infarction Biomarker for heart failure | Tamura et al., 2000 Hejmdal et al., 2007 Seferian et al., 2007 Doust et al., 2004 |
| Ttn Titin | ↓1.4 | Cardiac muscle dystrophies (contractility) | Fougerousse et al., 1998; Koatin et al., 2000 |
| Cyr61 Cysteine rich protein 61 | ↓1.7 | Inflammatory cardiomyopathy | Wittchen et al., 2007; Mo and Lau, 2006 |
| Sgcb Sarcoglycan | | Cardiac muscle dystrophies | Fougerousse et al., 1998 |

TABLE 5

Results of Nell1 Protein Treatment of Damaged Heart Tissue in a Mouse Model with Myocardial Infarction

| Mouse Number | Weight Change 17 day period | Heart length Top-Bottom (mm) | Heart Width Left-Right (mm) | Heart Depth Front-Back (mm) | Estimated Infarct Size 17 days post-MI (% left ventricle) |
|---|---|---|---|---|---|
| Controls (PBS) | | | | | |
| m2589 | 0 | 8.32 | 5.84 | 4.91 | 75% |
| m2588 | +1.2 | 8.55 | 6.20 | 5.11 | 50% |
| m2733 | −0.9 | 8.78 | 7.01 | 5.69 | 60-70% |

TABLE 5-continued

Results of Nell1 Protein Treatment of Damaged Heart Tissue in a Mouse Model with Myocardial Infarction

| Mouse Number | Weight Change 17 day period | Heart length Top-Bottom (mm) | Heart Width Left-Right (mm) | Heart Depth Front-Back (mm) | Estimated Infarct Size 17 days post-MI (% left ventricle) |
|---|---|---|---|---|---|
| m2764 | +1.1 | 8.52 | 6.09 | 5.57 | 90% |
| Average Nell1 Protein Dose I (312 ng) | +0.35 | 8.54 | 6.28 | 5.32 | ~70% |
| m2550 | −3.2 | 8.42 | 7.41 | 6.19 | Infarct hardly visible until fixation; ~16% faint area |
| m2597 | −2.3 | 8.04 | 6.12 | 6.17 | Infarct barely visible until fixation; 30% faint area |
| m2553 | −2.3 | 9.21 | 6.44 | 5.52 | Infarct hardly visible until fixation; 30% faint area |
| Average Nell1 Protein Dose II (624 ng) | −2.6 | 8.56 | 6.66 | 5.96 | ~25.3% |
| m2668 | +0.1 | 8.51 | 6.55 | 5.65 | Infarct hardly visible until fixation; 25% faint area |
| m2732 | −0.1 | 8.94 | 6.44 | 5.73 | Infarct hardly visible until fixation; 10% very small faint area |
| m2726 | −2.7 | 8.50 | 6.90 | 5.94 | Infarct hardly visible until fixation; very faint layer difficult to estimate |
| m2727 | −0.3 | 8.42 | 6.95 | 6.26 | Visible infarct at ~30% |
| Average | −0.75 | 8.59 | 6.71 | 5.90 | ~16.3% |

REFERENCES

Aghaloo T et al. *Am. J of Path* 2006; 169:903-915.
Ahn D et al. *Am J Physiol Heart Circ Physiol* 2004, 286:1201-1207.
Baurand A et al, *Circ Res* 2007; 100:1353-1362.
Chen C L et al. *Biochim Biophys Acta* 2007; 1772: 317-329.
Coles B et al. *Am J Pathol* 2007; May 3 Epub.
Cundy T et al. *Hum Mol Genet* 2002; 11:2119-2127.
Denz C R et al. *Biochem Biophys Res Commun* 2004; 320: 1291-1297.
Desai J et al. *Hum Mol Genet* 2006; 15:1329-1341.
Doust J A et al. *Arch Intern Med* 2004; 164: 1978-1984.
Egan J R et al. *Biochim Biophys Acta* 2006; 1758:1043-1052.
Fougerousse F et al. *Genomics* 1998; 48:145-156.
Grahame R et al. *Ann Rheum Dis* 1981; 40:541-546.
Helmjdal A et al. *J Card Fail* 2007; 13:184-188.
Jackson G C et al. *J Med Genet* 2005; 41:52-59.
Kostin S et al. *Heart Fail Rev.* 200 5:271-280.
Koitabashi N et al. *Hypertension* 2007; 49:1120-1127.
Kuroda et al., *Biochemical Biophysical Research Comm.* 265: 79-86 (1999a).
Kuroda et al., *Biochemical Biophysical Research Comm.* 265: 752-757 (1999b).
Lai A C, et al. *J Cardiovasc Electrophysiol* 2000; 11: 1345-1351.
Leier C V et al. *Ann Intern Med* 1980, 92:171-178.
Lim D S et al. *J Am Coll Cardiol* 2001; 38:1175-1180
Liu L et al. *Journal of Undergraduate Research* (Vol. 7). 2007.
Lu et al. *The Spine Journal* 2007; 7: 50-60.
Mao J R et al. *J Clin Invest* 2001; 107: 1063-1069.
Mao J R et al. *Nat Genet* 2002; 30:421-425.
Mizuno T et al. *BMC Genet* 2001; 2: 8.
Mizuno Y et al. *Proc Natl Acad Sci U.S.A.* 2001; 98: 6156-6161.
Mo F E et al. *Circ. Res.* 2006; 99: 961-969.
Mu J et al. *Physiol Genomics* Jun. 5, 2007 (Epub).
Okamoto H. *Mol Cell Biochem* 2007; 300:1-7.
Orlic D et al. *Ann NY Acad Sci* 2001; 938:221-229.
Orlic D et al. *Nature* 2001; 410: 701-705.
Ott et al. *Expert Opin Biol Ther* 2006; 6(9): 867-78.
Patten R D et al. *Am J Physiol Heart Circ Physiol.* 1998; 274:1812-1820.
Rosenthal et al., *Cell Transplant* 2006; 15 Suppl 1: S41-5.
Rubart et al., *Ann NY Acad Sci* 2006; 1080: 34-48
Seferian K R et al. *Clin Chem* 2007; 53:866-873.
Sharma U C et al. *Circulation* 2004; 110:3121-3128.
Singh M et al. *Front Biosci* 2007; 12:214-221.
Stem cell repair in ischemic heart disease: an experimental model. *Int J Hematol.* 2002; 76 Suppl 1:144-145.
Sussman, *Nature* 2001; 410: 640-641.
Takemoto S et al. *Basic Res Cardiol* 2002; 97: 461-468.
Tamura et al. *Proc Natl Acad Sci USA* 2000; 97:4239-4244.
Tarnavski O et al. *Physiol Genomics* 2004; 16:349-360.
Terrell et al. *Shock* 2006; 26:226-234.
Terasaki F et al. *Circ J* 2007; 71:327-330.
Ting K. et al. *J of Bone and Mineral Research* 1999; 14:80-88.
van Kimmenade et al. *J. Am. Coll. Cardiol.* 2006; 48: 1217-1224
Weiss R M et al. *Circulation* 2006; 114: 2065-2069.
Wernicke D et al. *Biomed Tech* (Berl) 2007; 52: 50-55
Wittchen F et al. *J Mol Med* 2007; 85:253-267.
Zhang X et al. *J Bone Miner Res* 2003; 18:2126-2134.
Zhang X et al. *J Clin Invest* 2002; 110:861-870.

What is claimed is:

1. A method of retarding progression or ameliorating symptoms of a cardiovascular disorder in a subject in need thereof comprising administering a Nell1 protein to said subject, wherein said cardiovascular disorder is myocardial infarction, and wherein said Nell1 protein has an amino acid sequence having at least 85% sequence identity to SEQ ID NO: 2, 4, or 6 and stimulates differentiation of cardiomyocyte precursor cells.

2. A method of retarding progression or ameliorating symptoms of a cardiovascular disorder in a subject in need thereof comprising administering a nucleic acid coding for a Nell1 protein to said subject, wherein said cardiovascular disorder is myocardial infarction, and wherein said nucleic acid is selected from the group consisting of:
   a) a nucleic acid coding for a Nell1 protein that has an amino acid sequence having at least 85% sequence identity to SEQ ID NO: 2, 4, or 6 and stimulates differentiation of cardiomyocyte precursor cells; and
   b) a nucleic acid having the sequence set forth in SEQ ID NO: 1, 3, or 5; and
   wherein said nucleic acid is in an expression vector to effect expression of Nell1 in said subject.

3. The method of claim 1 or 2, wherein said Nell1 protein comprises an amino acid sequence as set forth in any one of SEQ ID NO: 2, SEQ ID NO: 4 or SEQ ID NO: 6.

4. The method of claim 2, wherein said expression vector is a viral or non-viral vector.

5. The method of claim 1 or 2, wherein said Nell1 protein or said nucleic acid is administered systemically.

6. The method of claim 5, wherein said Nell1 protein or said nucleic acid is administered by ingestion, injection or implantation.

7. The method of claim 1 or 2, wherein said Nell1 protein or said nucleic acid is administered locally.

8. The method of claim 7, wherein said Nell1 protein or said nucleic acid is administered by injection or implantation at or near the site of cardiac muscle damage.

9. The method of claim 1 or 2, wherein said Nell1 protein or said nucleic acid is administered via catheter to or near the site of cardiac muscle damage.

10. The method of claim 1 or 2, wherein said Nell1 protein or said nucleic acid is administered in conjunction with cells for the repair and regeneration of damaged cardiac muscles and blood vessels.

11. The method of claim 10, wherein said cells are cardiomyocytes.

12. The method of claim 10, wherein said cells are stem cells.

13. The method of claim 1, wherein said Nell1 protein has an amino acid sequence having at least 95% sequence identity to SEQ ID NO: 2, 4, or 6 and stimulates differentiation of cardiomyocyte precursor cells.

14. The method of claim 2, wherein said a nucleic acid codes for a Nell1 protein that has an amino acid sequence having at least 95% sequence identity to SEQ ID NO: 2, 4, or 6 and stimulates differentiation of cardiomyocyte precursor cells.

* * * * *

SEQUENCE LISTING

<160> NUMBER OF SEQ ID NOS: 6

<210> SEQ ID NO 1
<211> LENGTH: 2966
<212> TYPE: DNA
<213> ORGANISM: Homo sapiens

<400> SEQUENCE: 1

| | | | | | |
|---|---|---|---|---|---|
| ggcgctgccg | agccacctcc | cccgccgccc | gctagcaagt | ttggcggctc | caagccaggc | 60 |
| gcgcctcagg | atccaggctc | atttgcttcc | acctagcttc | ggtgcccct | gctaggcggg | 120 |
| gaccctcgag | agcgatgccg | atggatttga | ttttagttgt | gtggttctgt | gtgtgcactg | 180 |
| ccaggacagt | ggtgggcttt | gggatggacc | ctgaccttca | gatggatatc | gtcaccgagc | 240 |
| ttgaccttgt | gaacaccacc | cttggagttg | ctcaggtgtc | tggaatgcac | aatgccagca | 300 |
| aagcattttt | atttcaagac | atagaaagag | agatccatgc | agctcctcat | gtgagtgaga | 360 |
| aattaattca | gctgttccag | aacaagagtg | aattcaccat | tttggccact | gtacagcaga | 420 |
| tggagagcag | tggcctgagg | gatgagattc | ggtatcacta | catacacaat | gggaagccaa | 480 |
| ggacagaggc | acttccttac | cgcatggcag | atggacaatg | cacaaggtt | gcactgtcag | 540 |
| ttagcgcctc | tcatctcctg | ctccatgtcg | actgtaacag | gatttatgag | cgtgtgatag | 600 |
| accctccaga | taccaacctt | cccccaggaa | tcaatttatg | gcttggccag | cgcaaccaaa | 660 |
| agcatggctt | attcaagggg | atcatccaag | atgggaagat | catctttatg | ccgaatggat | 720 |
| atataacaca | gtgtccaaat | ctaaatcaca | cttgcccaac | ctgcagtgat | ttcttaagcc | 780 |
| tggtgcaagg | aataatggat | ttacaagagc | ttttggccaa | gatgactgca | aaactaaatt | 840 |
| atgcagagac | aagacttagt | caattggaaa | actgtcattg | tgagaagact | tgtcaagtga | 900 |
| gtggactgct | ctatcgagat | caagactctt | gggtagatgg | tgaccattgc | aggaactgca | 960 |
| cttgcaaaag | tggtgccgtg | aatgccgaa | ggatgtcctg | tcccctctc | aattgctccc | 1020 |
| cagactccct | cccagtgcac | attgctggcc | agtgctgtaa | ggtctgccga | ccaaaatgta | 1080 |
| tctatgagg | aaaagttctt | gcagaaggcc | agcggatttt | aaccaagagc | tgtcgggaat | 1140 |
| gccgaggtgg | agttttagta | aaaattacag | aaatgtgtcc | tcctttgaac | tgctcagaaa | 1200 |
| aggatcacat | tcttcctgag | aatcagtgct | gccgtgtctg | tagaggtcat | aacttttgtg | 1260 |
| cagaaggacc | taaatgtggt | gaaaactcag | agtgcaaaaa | ctggaataca | aaagctactt | 1320 |
| gtgagtgcaa | gagtggttac | atctctgtcc | agggagactc | tgcctactgt | gaagatattg | 1380 |
| atgagtgtgc | agctaagatg | cattactgtc | atgccaatac | tgtgtgtgtc | aaccttcctg | 1440 |
| ggttatatcg | ctgtgactgt | gtcccaggat | acattcgtgt | ggatgacttc | tcttgtacag | 1500 |
| aacacgatga | atgtggcagc | ggccagcaca | actgtgatga | aatgccatc | tgcaccaaca | 1560 |
| ctgtccaggg | acacagctgc | acctgcaaac | cgggctacgt | ggggaacggg | accatctgca | 1620 |
| gagctttctg | tgaagagggc | tgcagatacg | gtggaacgtg | tgtggctccc | aacaaatgtg | 1680 |
| tctgtccatc | tggattcaca | ggaagccact | gcgagaaaga | tattgatgaa | tgttcagagg | 1740 |
| gaatcattga | gtgccacaac | cattcccgct | gcgttaacct | gccagggtgg | taccactgtg | 1800 |
| agtgcagaag | cggtttccat | gacgatggga | cctattcact | gtccggggag | tcctgtattg | 1860 |
| acattgatga | atgtgcctta | agaactcaca | cctgttggaa | cgattctgcc | tgcatcaacc | 1920 |
| tggcaggggg | ttttgactgt | ctctgccccct | ctgggccctc | ctgctctggt | gactgtcctc | 1980 |
| atgaagggg | gctgaagcac | aatggccagg | tgtggaccct | gaaagaagac | aggtgttctg | 2040 |

-continued

```
tctgctcctg caaggatggc aagatattct gccgacggac agcttgtgat tgccagaatc    2100
caagtgctga cctattctgt tgcccagaat gtgacaccag agtcacaagt caatgtttag    2160
accaaaatgg tcacaagctg tatcgaagtg gagacaattg gacccatagc tgtcagcagt    2220
gtcggtgtct ggaaggagag gtagattgct ggccactcac ttgccccaac ttgagctgtg    2280
agtatacagc tatcttagaa ggggaatgtt gtccccgctg tgtcagtgac ccctgcctag    2340
ctgataacat cacctatgac atcagaaaaa cttgcctgga cagctatggt gtttcacggc    2400
ttagtggctc agtgtggacg atggctggat ctccctgcac aacctgtaaa tgcaagaatg    2460
gaagagtctg ttgttctgtg gattttgagt gtcttcaaaa taattgaagt atttacagtg    2520
gactcaacgc agaagaatgg acgaaatgac catccaacgt gattaaggat aggaatcggt    2580
agtttggttt ttttgtttgt tttgtttttt taaccacaga taattgccaa agtttccacc    2640
tgaggacggt gtttggaggt tgccttttgg acctaccact ttgctcattc ttgctaacct    2700
agtctaggtg acctacagtg ccgtgcattt aagtcaatgg ttgttaaaag aagtttcccg    2760
tgttgtaaat catgtttccc ttatcagatc atttgcaaat acatttaaat gatctcatgg    2820
taaatgttga tgtattttttt ggtttatttt gtgtactaac ataatagaga gagactcagc    2880
tccttttatt tattttgttg atttatggat caaattctaa aataaagttg cctgttgtga    2940
aaaaaaaaaa aaaaaaaaa aaaaaa                                          2966
```

<210> SEQ ID NO 2
<211> LENGTH: 810
<212> TYPE: PRT
<213> ORGANISM: Homo sapiens

<400> SEQUENCE: 2

```
Met Pro Met Asp Leu Ile Leu Val Val Trp Phe Cys Val Cys Thr Ala
1               5                   10                  15

Arg Thr Val Val Gly Phe Gly Met Asp Pro Asp Leu Gln Met Asp Ile
                20                  25                  30

Val Thr Glu Leu Asp Leu Val Asn Thr Thr Leu Gly Val Ala Gln Val
            35                  40                  45

Ser Gly Met His Asn Ala Ser Lys Ala Phe Leu Phe Gln Asp Ile Glu
        50                  55                  60

Arg Glu Ile His Ala Ala Pro His Val Ser Glu Lys Leu Ile Gln Leu
65                  70                  75                  80

Phe Arg Asn Lys Ser Glu Phe Thr Ile Leu Ala Thr Val Gln Gln Lys
                85                  90                  95

Pro Ser Thr Ser Gly Val Ile Leu Ser Ile Arg Glu Leu Glu His Ser
            100                 105                 110

Tyr Phe Glu Leu Glu Ser Ser Gly Leu Arg Asp Glu Ile Arg Tyr His
        115                 120                 125

Tyr Ile His Asn Gly Lys Pro Arg Thr Glu Ala Leu Pro Tyr Arg Met
    130                 135                 140

Ala Asp Gly Gln Trp His Lys Val Ala Leu Ser Val Ser Ala Ser His
145                 150                 155                 160

Leu Leu Leu His Val Asp Cys Asn Arg Ile Tyr Glu Arg Val Ile Asp
                165                 170                 175

Pro Pro Asp Thr Asn Leu Pro Pro Gly Ile Asn Leu Trp Leu Gly Gln
            180                 185                 190

Arg Asn Gln Lys His Gly Leu Phe Lys Gly Ile Ile Gln Asp Gly Lys
        195                 200                 205

Ile Ile Phe Met Pro Asn Gly Tyr Ile Thr Gln Cys Pro Asn Leu Asn
```

```
                210                 215                 220
His Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Ser Gln Leu Glu Asn Cys His Cys Glu Lys Thr
                260                 265                 270

Cys Gln Val Ser Gly Leu Leu Tyr Arg Asp Gln Asp Ser Trp Val Asp
                275                 280                 285

Gly Asp His Cys Arg Asn Cys Thr Cys Lys Ser Gly Ala Val Glu Cys
290                 295                 300

Arg Arg Met Ser Cys Pro Leu Asn Cys Ser Pro Asp Ser Leu Pro
305                 310                 315                 320

Val His Ile Ala Gly Gln Cys Cys Lys Val Cys Arg Pro Lys Cys Ile
                325                 330                 335

Tyr Gly Gly Lys Val Leu Ala Glu Gly Gln Arg Ile Leu Thr Lys Ser
                340                 345                 350

Cys Arg Glu Cys Arg Gly Gly Val Leu Val Lys Ile Thr Glu Met Cys
                355                 360                 365

Pro Pro Leu Asn Cys Ser Glu Lys Asp His Ile Leu Pro Glu Asn Gln
370                 375                 380

Cys Cys Arg Val Cys Arg Gly His Asn Phe Cys Ala Glu Gly Pro Lys
385                 390                 395                 400

Cys Gly Glu Asn Ser Glu Cys Lys Asn Trp Asn Thr Lys Ala Thr Cys
                405                 410                 415

Glu Cys Lys Ser Gly Tyr Ile Ser Val Gln Gly Asp Ser Ala Tyr Cys
                420                 425                 430

Glu Asp Ile Asp Glu Cys Ala Ala Lys Met His Tyr Cys His Ala Asn
                435                 440                 445

Thr Val Cys Val Asn Leu Pro Gly Leu Tyr Arg Cys Asp Cys Val Pro
450                 455                 460

Gly Tyr Ile Arg Val Asp Asp Phe Ser Cys Thr Glu His Asp Glu Cys
465                 470                 475                 480

Gly Ser Gly Gln His Asn Cys Asp Glu Asn Ala Ile Cys Thr Asn Thr
                485                 490                 495

Val Gln Gly His Ser Cys Thr Cys Lys Pro Gly Tyr Val Gly Asn Gly
                500                 505                 510

Thr Ile Cys Arg Ala Phe Cys Glu Glu Gly Cys Arg Tyr Gly Gly Thr
                515                 520                 525

Cys Val Ala Pro Asn Lys Cys Val Cys Pro Ser Gly Phe Thr Gly Ser
                530                 535                 540

His Cys Glu Lys Asp Ile Asp Glu Cys Ser Glu Gly Ile Ile Glu Cys
545                 550                 555                 560

His Asn His Ser Arg Cys Val Asn Leu Pro Gly Trp Tyr His Cys Glu
                565                 570                 575

Cys Arg Ser Gly Phe His Asp Asp Gly Thr Tyr Ser Leu Ser Gly Glu
                580                 585                 590

Ser Cys Ile Asp Ile Asp Glu Cys Ala Leu Arg Thr His Thr Cys Trp
                595                 600                 605

Asn Asp Ser Ala Cys Ile Asn Leu Ala Gly Gly Phe Asp Cys Leu Cys
                610                 615                 620

Pro Ser Gly Pro Ser Cys Ser Gly Asp Cys Pro His Glu Gly Gly Leu
625                 630                 635                 640
```

```
Lys His Asn Gly Gln Val Trp Thr Leu Lys Glu Asp Arg Cys Ser Val
                645                 650                 655

Cys Ser Cys Lys Asp Gly Lys Ile Phe Cys Arg Arg Thr Ala Cys Asp
            660                 665                 670

Cys Gln Asn Pro Ser Ala Asp Leu Phe Cys Pro Glu Cys Asp Thr
                675                 680                 685

Arg Val Thr Ser Gln Cys Leu Asp Gln Asn Gly His Lys Leu Tyr Arg
                690                 695                 700

Ser Gly Asp Asn Trp Thr His Ser Cys Gln Gln Cys Arg Cys Leu Glu
705                 710                 715                 720

Gly Glu Val Asp Cys Trp Pro Leu Thr Cys Pro Asn Leu Ser Cys Glu
                725                 730                 735

Tyr Thr Ala Ile Leu Glu Gly Glu Cys Cys Pro Arg Cys Val Ser Asp
                740                 745                 750

Pro Cys Leu Ala Asp Asn Ile Thr Tyr Asp Ile Arg Lys Thr Cys Leu
                755                 760                 765

Asp Ser Tyr Gly Val Ser Arg Leu Ser Gly Ser Val Trp Thr Met Ala
                770                 775                 780

Gly Ser Pro Cys Thr Thr Cys Lys Cys Lys Asn Gly Arg Val Cys Cys
785                 790                 795                 800

Ser Val Asp Phe Glu Cys Leu Gln Asn Asn
                805                 810

<210> SEQ ID NO 3
<211> LENGTH: 2752
<212> TYPE: DNA
<213> ORGANISM: Mus musculus

<400> SEQUENCE: 3
gcgttggtgc gccctgcttg gcggggggcc tccggagcga tgccgatgga tgtgatttta    60
gttttgtggt tctgtgtgtg caccgccagg acagtgctgg gctttgggat ggaccctgac   120
cttcagatgg acatcatcac tgaacttgac cttgtgaaca ccaccctggg cgtcactcag   180
gtggctggac tacacaatgc cagtaaggca tttctgtttc aagatgtaca gagagagatc   240
cactcagccc ctcatgtgag tgagaagctg atccagctat tccggaataa gagtgagttt   300
acctttttgg ctacagtgca gcagaagccg tccacctcag gggtgatact gtcgatccgg   360
gagctggaac acagctattt tgaactggag agcagtggcc aagagaaga gatacgctat   420 cattacatcc atggcggcaa gcccaggact gaggcccttc cctaccgcat ggccgatgga   480
cagtggcaca aggtcgcgct gtctgtgagc gcctctcacc tcctactcca tgtcgactgc   540
aataggattt atgagcgtgt gatagatcct ccggagacca accttcctcc aggaagcaat   600
aagatcatct tcatgccgaa cggcttcatc acacagtgcc caacctaaa tcgcacttgc   660 ccaacatgca gtgatttcct gagcctggtt caaggaataa tggatttgca agagcttttg   720
gccaagatga ctgcaaaact gaattatgca gagacgagac ttggtcaact ggaaaattgc   780
cactgtgaga agacctgcca agtgagtggg ctgctctaca gggaccaaga ctcctgggta   840
gatggtgaca actgcaggaa ctgcacatgc aaaagtggtg ctgtggagtg ccgaaggatg   900
tcctgtcccc cactcaactg ttccccagac tcacttcctg tgcatatttc tggccaatgt   960
tgtaaagttt gcagaccaaa atgtatctat ggaggaaaag ttcttgctga gggccagcgg  1020
attttaacca agacctgccg ggaatgtcga ggtggagtct tggtaaaaat cacagaagct  1080
tgccctcctt tgaactgctc agagaaggat catattcttc cggagaacca gtgctgcagg  1140
gtctgccgag gtcataactt ctgtgcagaa gcacctaagt gtggagaaaa actcggaatgc  1200
```

| | |
|---|---|
| aaaaattgga atacaaaagc gacttgtgag tgcaagaatg gatacatctc tgtccagggc | 1260 |
| aactctgcat actgtgaaga tatcgatgag tgtgcagcaa agatgcacta ctgtcatgcc | 1320 |
| aacacggtgt gtgtcaactt gccggggtta tatcgctgtg actgcatccc aggatacatc | 1380 |
| cgtgtggatg acttctcttg tacggagcat gatgattgtg gcagcggaca cacaactgt | 1440 |
| gacaaaaatg ccatctgtac caacacagtc cagggacaca gctgtacctg ccagccaggc | 1500 |
| tacgtgggaa atggtactgt ctgcaaagca ttctgtgaag agggttgcag atacggaggt | 1560 |
| acctgtgtgg cccctaacaa atgtgtctgt ccttctggat tcacaggaag ccactgtgag | 1620 |
| aaagatattg atgaatgtgc agagggattc gttgagtgcc acaaccactc ccgctgcgtt | 1680 |
| aaccttccag ggtggtacca ctgtgagtgc agaagcggtt ccatgacga tgggacctat | 1740 |
| tcactgtccg gggagtcctg cattgatatt gatgaatgtg ccttaagaac tcacacttgt | 1800 |
| tggaatgact ctgcctgcat caacttagca ggaggatttg actgcctgtg tccctctggg | 1860 |
| ccctcctgct ctggtgactg tccccacgaa gggggctga agcataatgg gcaggtgtgg | 1920 |
| attctgagag aagacaggtg ttcagtctgt tcctgtaagg atgggaagat attctgccgg | 1980 |
| cggacagctt gtgattgcca gaatccaaat gttgaccttt tctgctgccc agagtgtgac | 2040 |
| accagggtca ctagccaatg tttagatcaa agcggacaga agctctatcg aagtggagac | 2100 |
| aactggaccc acagctgcca gcagtgccga tgtctggaag agaggcaga ctgctggcct | 2160 |
| ctagcttgcc ctagtttgag ctgtgaatac acagccatct ttgaaggaga gtgttgtccc | 2220 |
| cgctgtgtca gtgaccccctg cctggctgat aatattgcct atgacatcag aaaaacttgc | 2280 |
| ctggacagct ctggtatttc gaggctgagc ggcgcagtgt ggacaatggc tggatctccc | 2340 |
| tgtacaacct gtcaatgcaa gatgggaga gtctgctgct ctgtggatct ggtgtgtctt | 2400 |
| gagaataact gaagatttta aatggactca tcacatgaga aaatggacaa aatgaccatc | 2460 |
| caacctgagg aagaggaggg gctgatttct ttttcttttt aaccacagtc aattaccaaa | 2520 |
| gtctccatca gaggaaggcg tttgggttgc ctttaccact ttgctcatcc ttgctgacct | 2580 |
| agtctagatg cctgcagtac cgtgtatttc ggtcgatggt tgttgagtct ccgtgctgta | 2640 |
| aatcacattt cccttgtcag atcatttaca gatacattta aaggattcca tgataaatgt | 2700 |
| taaagtacct tttgtttatt ttgtgtacca acataataga gacttggcac ca | 2752 |

<210> SEQ ID NO 4
<211> LENGTH: 810
<212> TYPE: PRT
<213> ORGANISM: Mus musculus

<400> SEQUENCE: 4

Met Pro Met Asp Val Ile Leu Val Leu Trp Phe Cys Val Cys Thr Ala
1               5                   10                  15

Arg Thr Val Leu Gly Phe Gly Met Asp Pro Asp Leu Gln Met Asp Ile
            20                  25                  30

Ile Thr Glu Leu Asp Leu Val Asn Thr Thr Leu Gly Val Thr Gln Val
        35                  40                  45

Ala Gly Leu His Asn Ala Ser Lys Ala Phe Leu Phe Gln Asp Val Gln
    50                  55                  60

Arg Glu Ile His Ser Ala Pro His Val Ser Glu Lys Leu Ile Gln Leu
65                  70                  75                  80

Phe Arg Asn Lys Ser Glu Phe Thr Phe Leu Ala Thr Val Gln Gln Lys
                85                  90                  95

Pro Ser Thr Ser Gly Val Ile Leu Ser Ile Arg Glu Leu Glu His Ser

```
                    100                 105                 110
Tyr Phe Glu Leu Glu Ser Ser Gly Pro Arg Glu Ile Arg Tyr His
                115                 120                 125
Tyr Ile His Gly Gly Lys Pro Arg Thr Glu Ala Leu Pro Tyr Arg Met
            130                 135                 140
Ala Asp Gly Gln Trp His Lys Val Ala Leu Ser Val Ser Ala Ser His
145                 150                 155                 160
Leu Leu Leu His Val Asp Cys Asn Arg Ile Tyr Glu Arg Val Ile Asp
                165                 170                 175
Pro Pro Glu Thr Asn Leu Pro Pro Gly Ser Asn Leu Trp Leu Gly Gln
                180                 185                 190
Arg Asn Gln Lys His Gly Phe Phe Lys Gly Ile Ile Gln Asp Gly Lys
                195                 200                 205
Ile Ile Phe Met Pro Asn Gly Phe Ile Thr Gln Cys Pro Asn Leu Asn
                210                 215                 220
Arg Thr Cys Pro Thr Cys Ser Asp Phe Leu Ser Leu Val Gln Gly Ile
225                 230                 235                 240
Met Asp Leu Gln Glu Leu Leu Ala Lys Met Thr Ala Lys Leu Asn Tyr
                245                 250                 255
Ala Glu Thr Arg Leu Gly Gln Leu Glu Asn Cys His Cys Glu Lys Thr
                260                 265                 270
Cys Gln Val Ser Gly Leu Leu Tyr Arg Asp Gln Asp Ser Trp Val Asp
                275                 280                 285
Gly Asp Asn Cys Arg Asn Cys Thr Cys Lys Ser Gly Ala Val Glu Cys
                290                 295                 300
Arg Arg Met Ser Cys Pro Pro Leu Asn Cys Ser Pro Asp Ser Leu Pro
305                 310                 315                 320
Val His Ile Ser Gly Gln Cys Cys Lys Val Cys Arg Pro Lys Cys Ile
                325                 330                 335
Tyr Gly Gly Lys Val Leu Ala Glu Gly Gln Arg Ile Leu Thr Lys Thr
                340                 345                 350
Cys Arg Glu Cys Arg Gly Gly Val Leu Val Lys Ile Thr Glu Ala Cys
                355                 360                 365
Pro Pro Leu Asn Cys Ser Glu Lys Asp His Ile Leu Pro Glu Asn Gln
                370                 375                 380
Cys Cys Arg Val Cys Arg Gly His Asn Phe Cys Ala Glu Ala Pro Lys
385                 390                 395                 400
Cys Gly Glu Asn Ser Glu Cys Lys Asn Trp Asn Thr Lys Ala Thr Cys
                405                 410                 415
Glu Cys Lys Asn Gly Tyr Ile Ser Val Gln Gly Asn Ser Ala Tyr Cys
                420                 425                 430
Glu Asp Ile Asp Glu Cys Ala Ala Lys Met His Tyr Cys His Ala Asn
                435                 440                 445
Thr Val Cys Val Asn Leu Pro Gly Leu Tyr Arg Cys Asp Cys Ile Pro
                450                 455                 460
Gly Tyr Ile Arg Val Asp Asp Phe Ser Cys Thr Glu His Asp Asp Cys
465                 470                 475                 480
Gly Ser Gly Gln His Asn Cys Asp Lys Asn Ala Ile Cys Thr Asn Thr
                485                 490                 495
Val Gln Gly His Ser Cys Thr Cys Gln Pro Gly Tyr Val Gly Asn Gly
                500                 505                 510
Thr Val Cys Lys Ala Phe Cys Glu Glu Gly Cys Arg Tyr Gly Gly Thr
                515                 520                 525
```

```
Cys Val Ala Pro Asn Lys Cys Val Cys Pro Ser Gly Phe Thr Gly Ser
            530                 535                 540

His Cys Glu Lys Asp Ile Asp Glu Cys Ala Glu Gly Phe Val Glu Cys
545                 550                 555                 560

His Asn His Ser Arg Cys Val Asn Leu Pro Gly Trp Tyr His Cys Glu
            565                 570                 575

Cys Arg Ser Gly Phe His Asp Asp Gly Thr Tyr Ser Leu Ser Gly Glu
            580                 585                 590

Ser Cys Ile Asp Ile Asp Glu Cys Ala Leu Arg Thr His Thr Cys Trp
            595                 600                 605

Asn Asp Ser Ala Cys Ile Asn Leu Ala Gly Gly Phe Asp Cys Leu Cys
            610                 615                 620

Pro Ser Gly Pro Ser Cys Ser Gly Asp Cys Pro His Glu Gly Gly Leu
625                 630                 635                 640

Lys His Asn Gly Gln Val Trp Ile Leu Arg Glu Asp Arg Cys Ser Val
            645                 650                 655

Cys Ser Cys Lys Asp Gly Lys Ile Phe Cys Arg Arg Thr Ala Cys Asp
            660                 665                 670

Cys Gln Asn Pro Asn Val Asp Leu Phe Cys Cys Pro Glu Cys Asp Thr
            675                 680                 685

Arg Val Thr Ser Gln Cys Leu Asp Gln Ser Gly Gln Lys Leu Tyr Arg
            690                 695                 700

Ser Gly Asp Asn Trp Thr His Ser Cys Gln Gln Cys Arg Cys Leu Glu
705                 710                 715                 720

Gly Glu Ala Asp Cys Trp Pro Leu Ala Cys Pro Ser Leu Ser Cys Glu
            725                 730                 735

Tyr Thr Ala Ile Phe Glu Gly Glu Cys Cys Pro Arg Cys Val Ser Asp
            740                 745                 750

Pro Cys Leu Ala Asp Asn Ile Ala Tyr Asp Ile Arg Lys Thr Cys Leu
            755                 760                 765

Asp Ser Ser Gly Ile Ser Arg Leu Ser Gly Ala Val Trp Thr Met Ala
            770                 775                 780

Gly Ser Pro Cys Thr Thr Cys Gln Cys Lys Asn Gly Arg Val Cys Cys
785                 790                 795                 800

Ser Val Asp Leu Val Cys Leu Glu Asn Asn
            805                 810

<210> SEQ ID NO 5
<211> LENGTH: 2915
<212> TYPE: DNA
<213> ORGANISM: Rattus norvegicus

<400> SEQUENCE: 5
aagcactggt tcttgttag cgttggtgcg ccctgcttgg cggggttct ccggagcgat      60 gccgatggat gtgattttag ttttgtggtt ctgtgtatgc accgccagga cagtgttggg     120
ctttgggatg gaccctgacc ttcagctgga catcatctca gagctcgacc tggtgaacac     180
caccctggga gtcacgcagg tggctggact gcacaacgcc agtaaagcat ttctatttca     240
agatgtacag agagagatcc attcggcccc tcacgtgagt gagaagctga tccagctatt     300
ccggaataag agcgagttca ccttttttggc tacagtgcag cagaaaccat ccacctcagg     360
ggtgatactg tccatccggg agctggagca cagctatttt gaactggaga gcagtggccc     420
aagagaagag atacgctacc attacataca tggtggaaag cccaggactg aggcccttcc     480
ctaccgcatg gcagacggac aatggcacaa ggtcgcgctg tcagtgagcg cctctcacct     540
```

```
cctgctccac atcgactgca ataggattta cgagcgtgtg atagaccctc cggagaccaa    600
ccttcctcca ggaagcaatc tgtggcttgg gcaacgtaac caaaagcatg gcttttcaa     660 aggaatcatc caagatggta agatcatctt catgccgaat ggtttcatca cacagtgtcc    720
caacctcaat cgcacttgcc caacatgcag tgacttcctg agcctggttc aaggaataat    780
ggatttgcaa gagcttttgg ccaagatgac tgcaaaactg aattatgcag agacgagact    840
tggtcaactg gaaaattgcc actgtgagaa gacctgccaa gtgagtgggc tgctctacag    900
ggaccaagac tcctgggtgg atggtgacaa ctgtgggaac tgcacgtgca aagtggtgc     960 cgtggagtgc cgcaggatgt cctgtccccc gctcaactgt tccccggact cacttcctgt   1020
gcacatttcc ggccagtgtt gtaaagtttg cagaccaaaa tgtatctatg aggaaaagt    1080 tcttgctgag ggccagcgga ttttaaccaa gacctgccgg gaatgtcgag gtggagtctt   1140
ggtaaaaatc acagaagctt gccctccttt gaactgctca gcaaggatc atattcttcc    1200 agagaatcag tgctgcaggg tctgcccagg tcataacttc tgtgcagaag cacctaagtg   1260
cggagaaaac tcggaatgca aaaattggaa tacaaaagca acctgtgagt gcaagaatgg   1320
atacatctct gtccagggca actctgcata ctgtgaagat attgatgagt gtgcagctaa   1380
aatgcactat tgtcatgcca acaccgtgtg tgtcaacttg ccggggttgt atcgctgtga   1440
ctgcgtccca gggtacatcc gtgtggatga cttctcttgt acggagcatg atgattgtgg   1500
cagcggacaa cacaactgcg acaaaaatgc catctgtacc aacacagtcc agggacacag   1560
ctgcacctgc cagccgggtt acgtgggaaa tggcaccatc tgcaaagcat ctgtgaaga    1620 gggttgcaga tacggaggta cctgtgtggc tcctaacaag tgtgtctgtc cttctggatt   1680
cacgggaagc cactgtgaga agatattga tgaatgcgca gagggattcg ttgaatgcca    1740
caactactcc cgctgtgtta acctgccagg gtggtaccac tgtgagtgca gaagcggttt   1800
ccatgacgat gggacctact cactgtccgg ggagtcctgc attgatatcg atgaatgtgc   1860
cttaagaact cacacttgtt ggaatgactc tgcctgcatc aacttagcag gaggatttga   1920
ctgcctgtgt ccctctgggc cctcctgctc tggtgactgt ccccacgaag gagggctgaa   1980
gcataatggg caggtgtgga ttctgagaga agacaggtgt tcagtctgtt cctgcaagga   2040
tgggaagata ttctgccggc ggacagcttg tgattgccag aatccaaatg ttgaccttt    2100 ttgctgccca gagtgcgata ccagggtcac cagccaatgt ttagatcaaa gtggacagaa   2160
gctctatcga agtggagaca actggaccca cagctgccag cagtgccgat gtctggaagg   2220
agaggcagac tgctggcctc tggcttgcc tagtttgggc tgtgaataca cagccatgtt   2280
tgaaggggag tgttgtcccc gatgtgtcag tgaccctgc ctggctggta atattgccta   2340
tgacatcaga aaaacttgcc tggacagctt tggtgtttcg aggctgagcg gagccgtgtg   2400
gacaatggct ggatctcctt gtacaacctg caaatgcaag aatgggagag tctgctgctc   2460
tgtggatctg gagtgtattg agaataactg aagattttaa atggactcgt cacgtgagaa   2520
aatgggcaaa atgatcatcc cacctgagga agaagagggg ctgatttctt tttcttttta   2580
accacagtca attaccaaag tctccatctg aggaaggcgt ttggattgcc tttgccactt   2640
tgctcatcct tgctgaccta gtctagatgc ctgcagtacc gtgcatttcg gtcgatggtt   2700
gttgagtctc agtgttgtaa atcgcatttc cctcgtcaga tcatttacag atacatttaa   2760
aggggttcca tgataaatgt taatgtaact tttgtttatt ttgtgtactg acataataga   2820
gacttggcac catttatta tttttcttga tttttggatc aaattctaaa aataaagttg     2880
cctgttgcga aaaaaaaaa aaaaaaaaaa aaaaa                                2915
```

```
<210> SEQ ID NO 6
<211> LENGTH: 802
<212> TYPE: PRT
<213> ORGANISM: Rattus norvegicus

<400> SEQUENCE: 6

Met Pro Met Asp Val Ile Leu Val Leu Trp Phe Cys Val Cys Thr Ala
1               5                   10                  15

Arg Thr Val Leu Gly Phe Gly Met Asp Pro Asp Leu Gln Leu Asp Ile
            20                  25                  30

Ile Ser Glu Leu Asp Leu Val Asn Thr Thr Leu Gly Val Thr Gln Val
        35                  40                  45

Ala Gly Leu His Asn Ala Ser Lys Ala Phe Leu Phe Gln Asp Val Gln
    50                  55                  60

Arg Glu Ile His Ser Ala Pro His Val Ser Glu Lys Leu Ile Gln Leu
65                  70                  75                  80

Phe Arg Asn Lys Ser Glu Phe Thr Phe Leu Ala Thr Val Gln Gln Lys
                85                  90                  95

Pro Ser Thr Ser Gly Val Ile Leu Ser Ile Arg Glu Leu Glu His Ser
            100                 105                 110

Tyr Phe Glu Leu Glu Ser Ser Gly Pro Arg Glu Glu Ile Arg Tyr His
        115                 120                 125

Tyr Ile His Gly Gly Lys Pro Arg Thr Glu Ala Leu Pro Tyr Arg Met
    130                 135                 140

Ala Asp Gly Gln Trp His Lys Val Ala Leu Ser Val Ser Ala Ser His
145                 150                 155                 160

Leu Leu Leu His Ile Asp Cys Asn Arg Ile Tyr Glu Arg Val Ile Asp
                165                 170                 175

Pro Pro Glu Thr Asn Leu Pro Pro Gly Ser Asn Leu Trp Leu Gly Gln
            180                 185                 190

Arg Asn Gln Lys His Gly Phe Phe Lys Gly Ile Ile Gln Asp Gly Lys
        195                 200                 205

Ile Ile Phe Met Pro Asn Gly Phe Ile Thr Gln Cys Pro Asn Leu Asn
    210                 215                 220

Arg Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Gly Gln Leu Glu Asn Cys His Cys Glu Lys Thr
            260                 265                 270

Cys Gln Val Ser Gly Leu Leu Tyr Arg Asp Gln Asp Ser Trp Val Asp
        275                 280                 285

Gly Asp Asn Cys Gly Asn Cys Thr Cys Lys Ser Gly Ala Val Glu Cys
    290                 295                 300

Arg Arg Met Ser Cys Pro Pro Leu Asn Cys Ser Pro Asp Ser Leu Pro
305                 310                 315                 320

Val His Ile Ser Gly Gln Cys Cys Lys Val Cys Arg Pro Lys Cys Ile
                325                 330                 335

Tyr Gly Gly Lys Val Leu Ala Glu Gly Gln Arg Ile Leu Thr Lys Thr
            340                 345                 350

Cys Arg Glu Cys Arg Gly Gly Val Leu Val Lys Ile Thr Glu Ala Cys
        355                 360                 365

Pro Pro Leu Asn Cys Ser Ala Lys Asp His Ile Leu Pro Glu Asn Gln
    370                 375                 380
```

-continued

```
Cys Cys Arg Val Cys Pro Gly His Asn Phe Cys Ala Glu Ala Pro Lys
385                 390                 395                 400

Cys Gly Glu Asn Ser Glu Cys Lys Asn Trp Asn Thr Lys Ala Thr Cys
                405                 410                 415

Glu Cys Lys Asn Gly Tyr Ile Ser Val Gln Gly Asn Ser Ala Tyr Cys
            420                 425                 430

Glu Asp Ile Asp Glu Cys Ala Ala Lys Met His Tyr Cys His Ala Asn
        435                 440                 445

Thr Val Cys Val Asn Leu Pro Gly Leu Tyr Arg Cys Asp Cys Val Pro
    450                 455                 460

Gly Tyr Ile Arg Val Asp Asp Phe Ser Cys Thr Glu His Asp Asp Cys
465                 470                 475                 480

Gly Ser Gly Gln His Asn Cys Asp Lys Asn Ala Ile Cys Thr Asn Thr
                485                 490                 495

Val Gln Gly His Ser Cys Thr Cys Gln Pro Gly Tyr Val Gly Asn Gly
            500                 505                 510

Thr Ile Cys Lys Ala Phe Cys Glu Glu Gly Cys Arg Tyr Gly Gly Thr
        515                 520                 525

Cys Val Ala Pro Asn Lys Cys Val Cys Pro Ser Gly Phe Thr Gly Ser
    530                 535                 540

His Cys Glu Lys Asp Ile Asp Glu Cys Ala Glu Gly Phe Val Glu Cys
545                 550                 555                 560

His Asn Tyr Ser Arg Cys Val Asn Leu Pro Gly Trp Tyr His Cys Glu
                565                 570                 575

Cys Arg Ser Gly Phe His Asp Asp Gly Thr Tyr Ser Leu Ser Gly Glu
            580                 585                 590

Ser Cys Ile Asp Ile Asp Glu Cys Ala Leu Arg Thr His Thr Cys Trp
        595                 600                 605

Asn Asp Ser Ala Cys Ile Asn Leu Ala Gly Gly Phe Asp Cys Leu Cys
    610                 615                 620

Pro Ser Gly Pro Ser Cys Ser Gly Asp Cys Pro His Glu Gly Gly Leu
625                 630                 635                 640

Lys His Asn Gly Gln Val Trp Ile Leu Arg Glu Asp Arg Cys Ser Val
                645                 650                 655

Cys Ser Cys Lys Asp Gly Lys Ile Phe Cys Arg Arg Thr Ala Cys Asp
            660                 665                 670

Cys Gln Asn Pro Asn Val Asp Leu Phe Cys Cys Pro Glu Cys Asp Thr
        675                 680                 685

Arg Val Thr Ser Gln Cys Leu Asp Gln Ser Gly Gln Lys Leu Tyr Arg
    690                 695                 700

Ser Gly Asp Asn Trp Thr His Ser Cys Gln Gln Cys Arg Cys Leu Glu
705                 710                 715                 720

Gly Glu Ala Asp Cys Trp Pro Leu Ala Cys Pro Ser Leu Gly Cys Glu
                725                 730                 735

Tyr Thr Ala Met Phe Glu Gly Glu Cys Cys Pro Arg Cys Val Ser Asp
            740                 745                 750

Pro Cys Leu Ala Gly Asn Ile Ala Tyr Asp Ile Arg Lys Thr Cys Leu
        755                 760                 765

Asp Ser Phe Gly Val Ser Arg Leu Ser Gly Ala Val Trp Thr Met Ala
    770                 775                 780

Gly Ser Pro Cys Thr Thr Cys Lys Cys Lys Asn Gly Arg Val Cys Cys
785                 790                 795                 800

Ser Val
```